: US008709232B2

United States Patent
Matzinger

(10) Patent No.: US 8,709,232 B2
(45) Date of Patent: Apr. 29, 2014

(54) ANALYTE MEASUREMENT TECHNIQUE AND SYSTEM

(75) Inventor: David Matzinger, Menlo Park, CA (US)

(73) Assignee: Cilag GmbH International, Zug (CH)

( * ) Notice: Subject to any disclaimer, the term of this patent is extended or adjusted under 35 U.S.C. 154(b) by 137 days.

(21) Appl. No.: 13/459,455

(22) Filed: Apr. 30, 2012

(65) Prior Publication Data

US 2013/0284611 A1    Oct. 31, 2013

(51) Int. Cl.
*G01N 27/26* (2006.01)
*G01N 33/50* (2006.01)

(52) U.S. Cl.
USPC ............. 205/777.5; 204/406; 204/403.01

(58) Field of Classification Search
USPC ............ 204/403.01–403.14, 406; 205/777.5
See application file for complete search history.

(56) References Cited

U.S. PATENT DOCUMENTS

| | | | | |
|---|---|---|---|---|
| 2007/0227912 A1* | 10/2007 | Chatelier et al. | | 205/792 |
| 2009/0184004 A1* | 7/2009 | Chatelier et al. | | 205/777.5 |
| 2009/0301899 A1* | 12/2009 | Hodges et al. | | 205/777.5 |
| 2011/0301857 A1* | 12/2011 | Huang et al. | | 702/19 |
| 2013/0220836 A1* | 8/2013 | Kermani et al. | | 205/782 |

FOREIGN PATENT DOCUMENTS

WO    WO 2012/012341 A1    1/2012

OTHER PUBLICATIONS

International Application No. PCT/US2013/038420, International Search Report dated Sep. 13, 2013, USPTO, 5 pages.

* cited by examiner

*Primary Examiner* — Luan Van
*Assistant Examiner* — Steven Rosenwald

(57) ABSTRACT

Described are methods and systems to apply a plurality of test voltages to the test strip and measure a current transient output resulting from an electrochemical reaction in a test chamber of the test strip so that highly accurate glucose concentration can be determined.

5 Claims, 18 Drawing Sheets

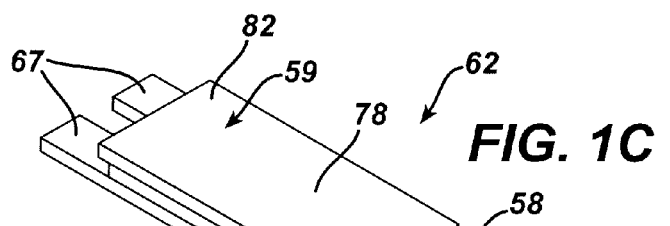
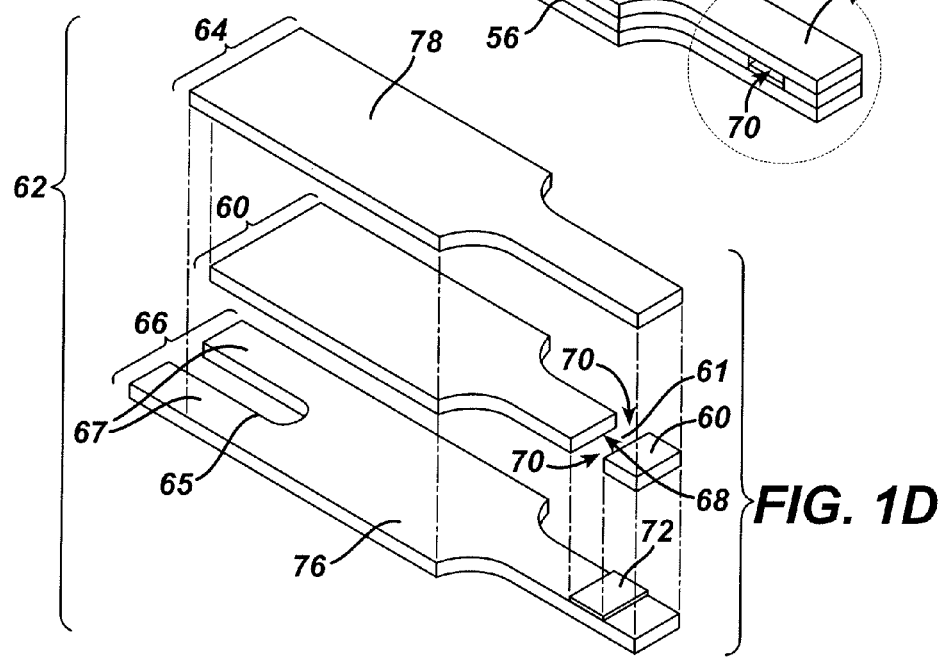
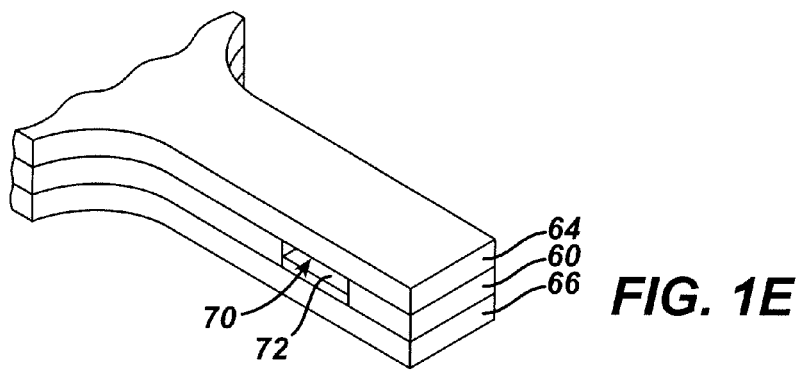

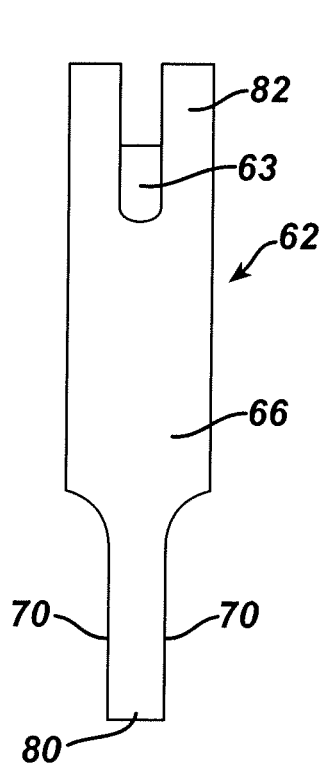 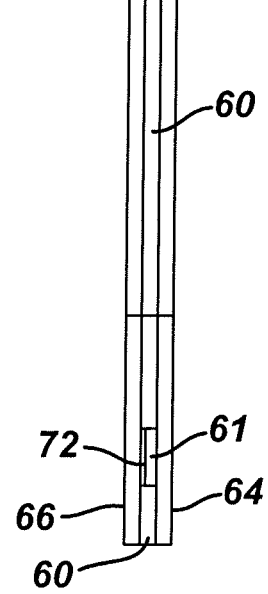 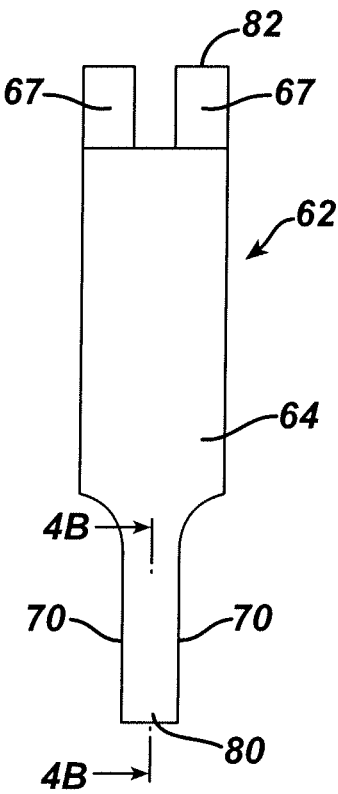
FIG. 2   FIG. 3   FIG. 4A
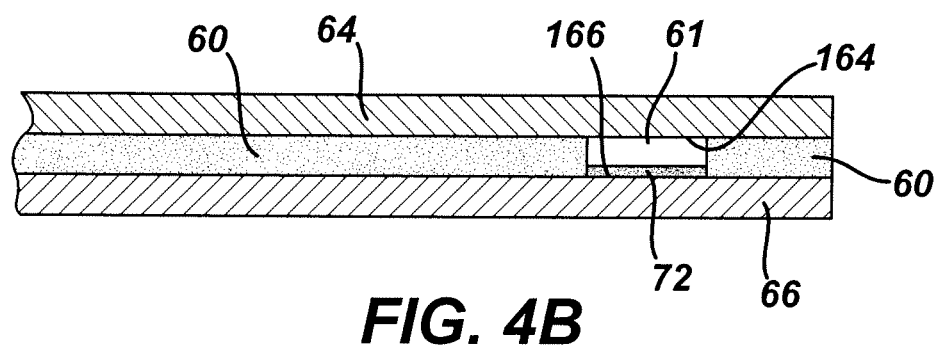
FIG. 4B

(Existing Technique)

(New Technique)
Glucose (G$_{basic}$' vs. uric acid)

FIG. 9C

Table IIA
Bias categorization, Pre-existing technique.
Data from uric acid study

| mg/dl glucose | 65 | 240 | 450 |
|---|---|---|---|
| | | | |
| 10 mg or 12% | 82.35% | 49.23% | 80.08% |
| 12 mg or 15% | 97.56% | 70.95% | 95.31% |
| 15 mg or 20% | 100.00% | 100.00% | 100.00% |

FIG. 9D

Table IIB
Bias categorization, New technique.
Data from uric acid study

| mg/dl glucose | 65 | 240 | 450 |
|---|---|---|---|
| | | | |
| 10 mg or 12% | 99.37% | 99.19% | 100.00% |
| 12 mg or 15% | 99.73% | 99.91% | 100.00% |
| 15 mg or 20% | 99.91% | 100.00% | 100.00% |

Bias vs. glucose, Pre-existing technique.
Data from uric acid study

Bias vs. glucose, New technique. Data from uric acid study

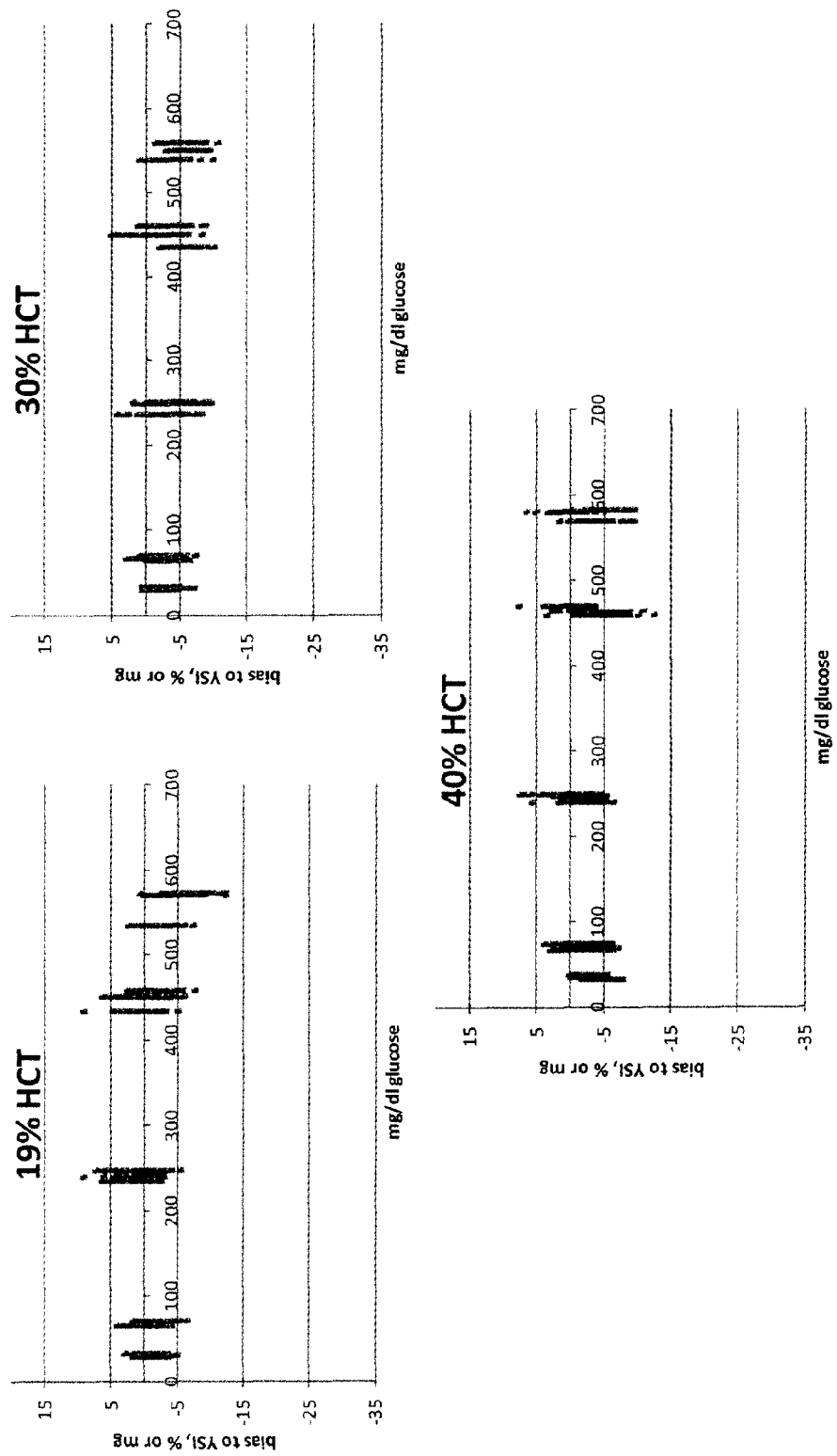
FIG. 11A(1)
Bias vs. glucose, Pre-existing technique.
Data from hematocrit study

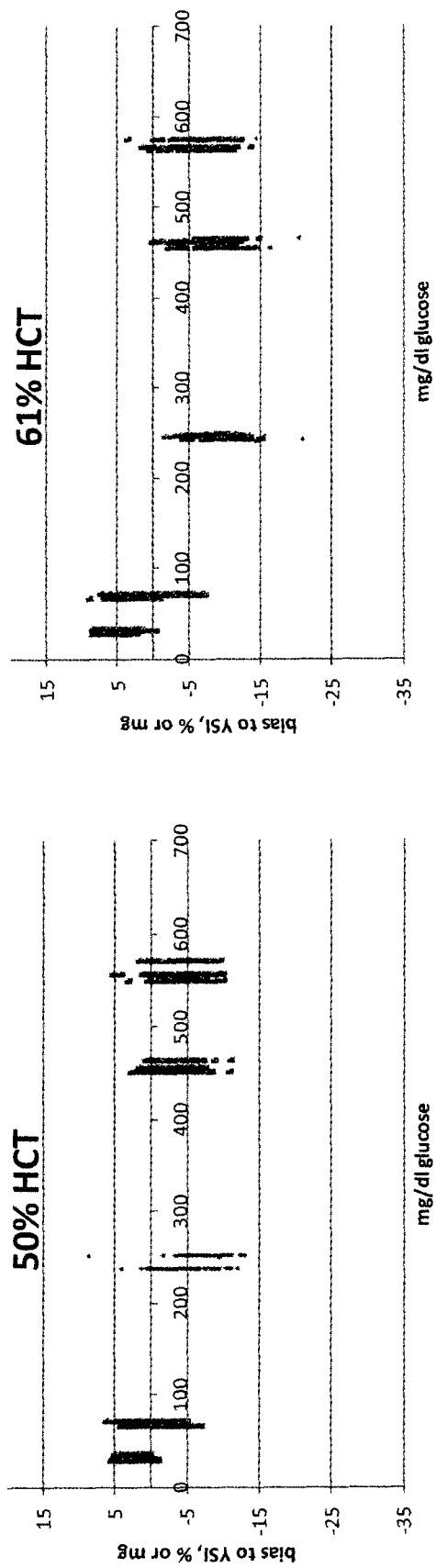
FIG. 11A(2)
Bias vs. glucose, Pre-existing technique.
Data from hematocrit study

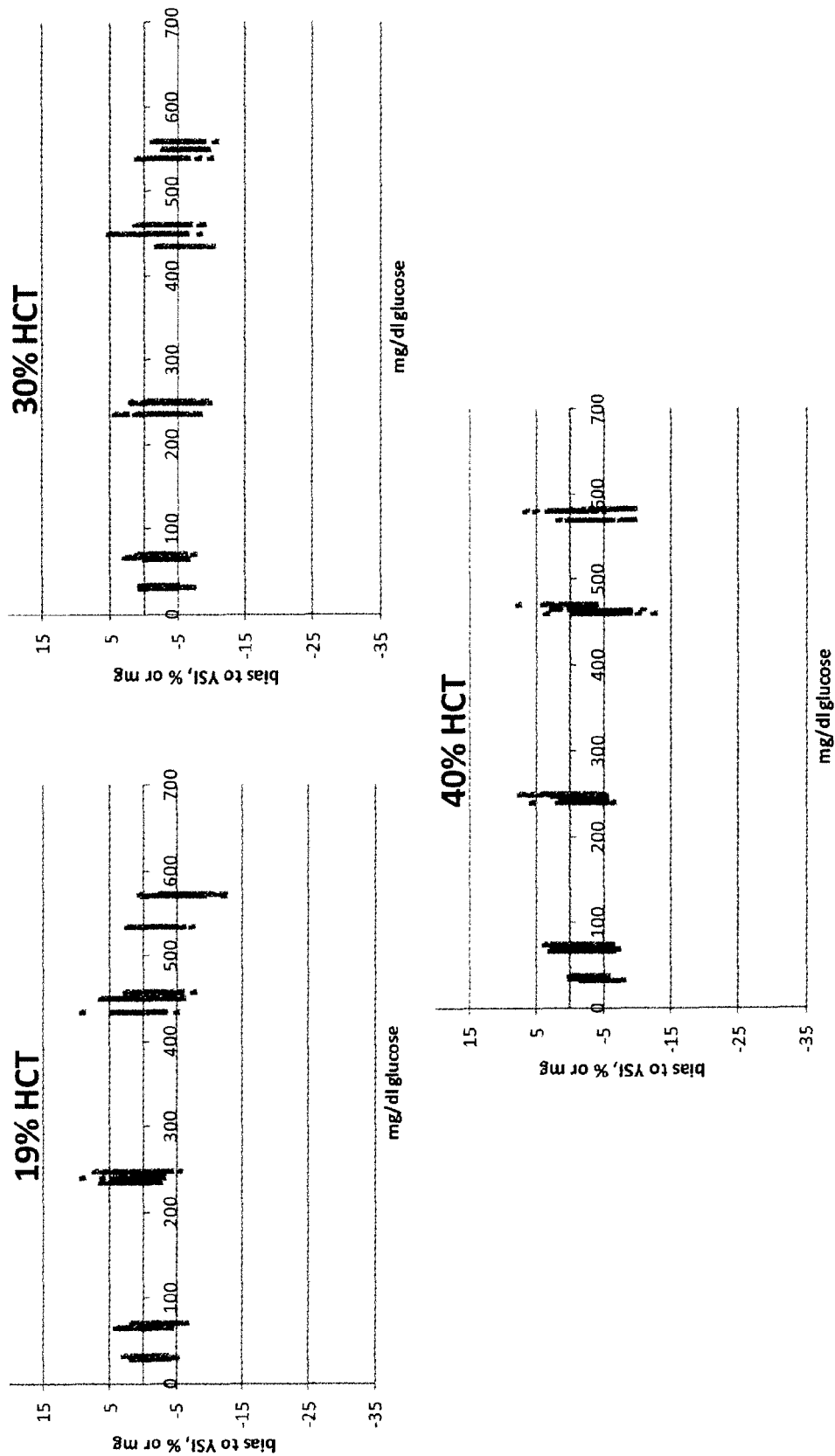
FIG. 11B(1)
Bias vs. glucose, New technique.
Data from hematocrit study

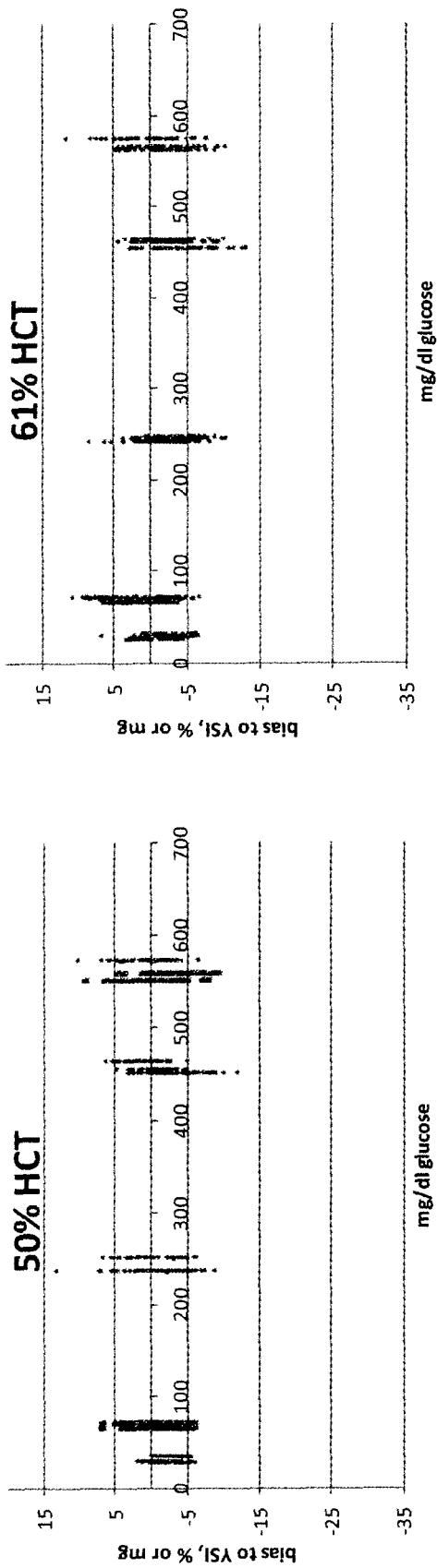

FIG. 12A

Table IIIA
Bias categorization, Pre-existing technique. Data from hematocrit study

| mg/dl glucose | 30-65 | 240 | 450-560 |
|---|---|---|---|
|  |  |  |  |
| 10 mg or 12% | 100.00% | 96.35% | 98.74% |
| 12 mg or 15% | 100.00% | 99.44% | 99.79% |
| 15 mg or 20% | 100.00% | 99.86% | 100.00% |

FIG. 12B

Table IIIB
Bias categorization, New technique. Data from hematocrit study

| mg/dl glucose | 30-65 | 240 | 450-560 |
|---|---|---|---|
|  |  |  |  |
| 10 mg or 12% | 100.00% | 99.62% | 99.80% |
| 12 mg or 15% | 100.00% | 99.81% | 100.00% |
| 15 mg or 20% | 100.00% | 100.00% | 100.00% |

ANALYTE MEASUREMENT TECHNIQUE AND SYSTEM

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency and/or error. One of the blood glucose measurement manufactured by LifeScan Inc., and marketed as One-Touch Verio ("Verio") has remarkably good overall performance with regards to resisting the effects of hematocrit and interfering reducing agents such as uric acid. Nevertheless, interferents such as reducing agents in the form of uric acid may affect the results of the method. Specifically, there is observed to be a potential hematocrit dependence from applicant's blood glucose data. As an example, consider a situation in which an electroactive species such as uric acid or ferrocyanide is uniformly distributed in the Verio test strip cell. Measurements taken immediately after switching potential are in a regime where the developing concentration gradient is semi-infinite: it has not yet moved out far enough into the cell that it is influenced by the gradient developing at the opposite electrode.

Another observation was the effect of endogenous reducing agents such as uric acid, independent of glucose. It is believed that Verio test strip uses the 1.1 second current to account for interferences by predicting the magnitude of interference current in the third pulse measurements based on the 1.1 second current:

$$i2corr = \left( \frac{|i4.1| + b|i5| - 2|i1.1|}{|i4.1| + b|i5|} \right) i_R \qquad (7)$$

where b~0.678

It would appear that this function is intended to find the fraction of $i_R$ that is due solely to glucose by using a function that goes to 1 if here is no interference ($i_{1.1}$=0) or 0 if there is interfering reducing agent current but no glucose ($i_{4.1}$, $i_5$ comprising only interference currents). If this is the case, i2corr should be independent of interfering reducing agent.

Experiments show that while i2corr does a good job of removing the uric acid dependence of iR at medium to high glucose, it does so incompletely at low glucose. But in spite of this fairly successful correction of $i_R$, the glucose results Gbasic (glucose results prior to correction(s)) are significantly influenced by uric acid, especially at high glucose.

The formula for glucose result is:

$$Gbasic = \left[ \frac{|i_R|}{|i_L|} \right]^p (a|i2corr| - zgr) \qquad (7.5)$$

Where
p~0.523
a~0.14
zgr~2

It is believed that while Gbasic has a strong uric acid dependence at high glucose, i2corr did not, and therefore it is apparent that the hematocrit compensation function is not working correctly when challenged with both high glucose and high interfering reducing agent levels. Part of this problem is undoubtedly due to the fact that $i_L$ (sum of current from 1.4 to 4 seconds) is strongly influenced by interfering reducing substances.

It is noted that $i_L$ is composed of an essentially steady state current from interfering reducing agents and a growing glucose current due to ongoing diffusion of ferrocyanide and enzyme from the second electrode. Uric acid has a substantially larger effect on $i_L$ than it does on $i_R$. The analysis above showed how the hematocrit compensation function should work by compensating for the effect of Red-Blood-Cells', assuming only glucose current was being detected. The hematocrit compensation function is really not designed to work correctly at different levels of interfering reducing agent. It is believed that what happens is that at high glucose, $i_L$ increases, causing inappropriately small values of the hematocrit compensation function and low glucose results.

Because |i2corr| increases with increasing uric agent, the effect of decreasing interference correction function is partially compensated. But no such compensation happens at high glucose, where i2corr works better. Thus it appears that there is an overcompensation for interfering reducing agents at high glucose, in reality the inputs to the hematocrit compensation function are being interfered with, causing incorrect hematocrit compensation.

SUMMARY OF THE DISCLOSURE

While the Verio system discussed previously has very good overall performance with regards to resisting the effects of hematocrit and interfering reducing agents such as uric acid, testing has shown, however, that Verio test strip is not completely impervious to interfering effects of endogenous and therapeutic reducing agents. These interferences are generally small at typical levels of interfering agents, but in light of the stringent performance requirements anticipated for glucose systems, it may be necessary to remove all possible sources of interference. In attempts to find ways to reduce interferences, applicant proposes to modify the glucose determination technique of such system without the need to modify the test strip chemistry. In particular, applicant has discovered parts of the technique causing less than optimal performance, and consequently made changes to improve the performance of the test strip and system.

Consequently, applicant has discovered various aspects of a method of calculating an analyte concentration of an analyte sample. In one aspect, a method of determining blood glucose concentration with a glucose measurement system that includes a test strip and test meter is provided. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; applying a first voltage; switching the first voltage to a second voltage different than the first voltage; changing the second voltage to a third voltage different from the second voltage; measuring a second current output of the current transient from the electrodes after the changing from the second voltage to the third voltage; estimating a current that approximates a steady state current output of the current transient after the third voltage is maintained at the electrodes; calculating a blood glucose concentration based on the first, second and third current output of the current transient with an equation of the form:

$$G_1 = \left(\frac{|i2corr'|}{|i'_L|}\right)^{p'}(a'|i2corr'| - zgr' + d);$$

where: $G_1$ includes a glucose concentration;

$$i_R = \sum_{t=4.4}^{t=5} i(t);$$

$$i'_L = \left(\sum_{t=1.4secs}^{t=4secs} i(t)\right) - 41(i_2);$$

$$i2corr' = \left(\frac{|i_{4.1}| + b'|i_5| - c|i_{1.1}|}{|i_{4.1}| + b'|i_5|}\right)i_R$$

where:
a', b', c, d, p', zgr' include manufacturing parameters;
$i_{4.1}$ includes the current measured during application of the third voltage;
$i_5$ includes the current measured during application of the third voltage;
$i_{1.1}$ includes the current measured during application of the second voltage; and
$i_2$ includes the current measured during application of the second voltage.

In this method, the measuring of the first current output includes measuring a current output of the at least two electrodes at about 1.1 seconds after initiation of the test sequence; the measuring of the second current output includes measuring a current output of the at least two electrodes at about 4.1 seconds after initiation of the test sequence; the estimating of the steady state current output includes measuring a current output of the at least two electrodes at about 5 seconds after initiation of the test sequence; the manufacturing parameter a' is approximately 0.14, b' is about approximately 4.9, c is about approximately 4.24, d is approximately 11.28, p' is about approximately 0.548, and zgr' is about approximately 9.38.

In yet another aspect, a method of determining blood glucose concentration with a glucose measurement system that includes a test strip and test meter is provided. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; applying a first voltage; causing a transformation of analytes in the sample from one form to a different form with reagent in the test chamber; switching the first voltage to a second voltage different than the first voltage; changing the second voltage to a third voltage different from the second voltage; measuring a second current output of the current transient from the electrodes after the changing from the second voltage to the third voltage; estimating a current that approximates a steady state current output of the current transient after the third voltage is maintained at the electrodes; deriving an initial glucose proportional current based on the first current, second current, and estimated current; formulating a hematocrit compensation factor based on the initial glucose proportional current; and calculating a glucose concentration from the derived initial glucose proportional current and the hematocrit compensation factor. In this particular method, the deriving includes calculating the initial glucose proportional current i2Corr' based on the following equation:

$$i2corr' = \left(\frac{|i_{4.1}| + b'|i_5| - c|i_{1.1}|}{|i_{4.1}| + b'|i_5|}\right)i_R$$

where i2Corr' includes the initial glucose proportional current, $i_{4.1}$ includes the current measured during the application of the third voltage, $i_5$ includes the current measured during the application of the third voltage; and $i_{1.1}$ includes the current measured during application of the second voltage; in which $i_{4.1}$ includes the current measured at about 4.1 seconds after initiation of the test sequence, $i_5$ includes the current measured at about 5 seconds after initiation of the test sequence; and $i_{1.1}$ includes the current measured at about 1.1 seconds after initiation of the test sequence; in which the hematocrit compensation factor includes a ratio of the initial glucose proportional current divided by an integration of current outputs during application of the second voltage less an offset based on a current output measured during application of the second voltage; the hematocrit compensation factor is of the form:

$$\left(\frac{|i2corr'|}{|i'_L|}\right)^{p'}$$

where p' includes a coefficient and $$i'_L = \left(\sum_{t=1.4secs}^{t=4secs} i(t)\right) - 41(i_2)$$

where $i_2$ includes a current measured at about 2 seconds after initiation of the test sequence and $41i_2$ includes the offset. The method further includes utilizing an equation of the form:

$$G_1 = \left(\frac{|i2corr'|}{|i'_L|}\right)^{'p}(a'|i2corr'| - zgr') + d;$$

where: $G_1$ includes a glucose concentration;

$$i_R = \sum_{t=4.4}^{t=5} i(t);$$

$$i'_L = \left(\sum_{t \sim 1.4\,secs}^{t \sim 4\,secs} i(t)\right) - 41(i_2);$$

$$i2corr' = \left(\frac{|i_{4.1}| + b'|i_5| - c|i_{1.1}|}{|i_{4.1}| + b'|i_5|}\right)i_R$$

where:
- a', b', c, d, p', zgr' include manufacturing parameters;
- $i_{4.1}$ includes the current measured during application of the third voltage and approximately 4.1 seconds after initiation of the test sequence;
- $i_5$ includes the current measured during application of the third voltage and approximately 5 seconds after initiation of the test sequence;
- $i_{1.1}$ includes the current measured during application of the second voltage and approximately 1.1 seconds after initiation of the test sequence; and
- $i_2$ includes the current measured during application of the second voltage and approximately 2 seconds after initiation of the test sequence.

In a further aspect, a blood glucose measurement system is provided that includes an analyte test strip and meter. The analyte test strip includes a substrate having a reagent disposed thereon; and at least two electrodes proximate the reagent in test chamber. The analyte meter includes a strip port connector disposed to connect to the two electrodes; a power supply; and a microcontroller electrically coupled to the strip port connector and the power supply, the microcontroller programmed to determine a glucose concentration $G_1$ based on a hematocrit compensation factor and initial glucose proportional current in which the hematocrit compensation factor includes a ratio that includes the initial glucose proportional current so that at least 97% of corrected test results are within respective bias criterion of ±10 mg/dL at 65 mg/dL, 240 mg/dL, or at 450 mg/dL as compared to reference YSI data; ±12 mg/dL at 65 mg/dL, 240 mg/dL, or 450 mg/dL as compared to reference YSI data; and ±15 mg/dL at 65 mg/dL, 240 mg/dL, or 450 mg/dL as compared to reference YSI data. In this system, the manufacturing parameters a', b', c, d, p', zgr' are such that a' is about approximately 0.14, b' is about approximately 4.9, c is about approximately 4.24, d is approximately 11.28 p' is about approximately 0.548 and zgr' is about approximately 9.38.

In yet a further aspect, a method of determining blood glucose concentration with a glucose measurement system that includes a test strip and test meter is provided. The test meter has a microcontroller configured to apply a plurality of test voltages to the test strip and measure a current transient output resulting from an electrochemical reaction in a test chamber of the test strip. The method can be achieved by initiating a test sequence after deposition of a sample; applying a first voltage; causing a transformation of analytes in the sample from one form to a different form with reagent in the test chamber; switching the first voltage to a second voltage different than the first voltage; changing the second voltage to a third voltage different from the second voltage; measuring a second current output of the current transient from the electrodes after the changing from the second voltage to the third voltage; estimating a current that approximates a steady state current output of the current transient after the third voltage is maintained at the electrodes; deriving an initial glucose proportional current based on the first current, second current, and estimated current; and formulating a hematocrit compensation factor based on the derived initial glucose proportional current. In this method, the formulating includes dividing the derived initial glucose proportional current by an integration of current outputs during application of the second voltage; the integration includes an offset to the integration based on a measured current during application of the second voltage. This method may further include the step of calculating a glucose concentration based on a compensation of the derived initial glucose proportional current with the hematocrit compensation factor; the hematocrit compensation factor is of the form:

$$\left(\frac{|i2corr'|}{|i'_L|}\right)^{p'}$$

where p' includes a coefficient and $$i'_L = \left(\sum_{t \sim 1.4\,sec\,s}^{t \sim 4\,sec\,s} i(t)\right) - 41(i_2)$$

where $i_2$ includes a current measured at about 2 seconds after initiation of the test sequence and $41i_2$ includes the offset. Alternatively, the calculating includes utilizing an equation of the form:

$$G_1 = \left(\frac{|i2corr'|}{|i'_L|}\right)^{'p}(a'|i2corr'| - zgr') + d;$$

where: $G_1$ includes a glucose concentration;

$$i_R = \sum_{t=4.4}^{t=5} i(t);$$

$$i'_L = \left(\sum_{t \sim 1.4\,sec\,s}^{t \sim 4\,sec\,s} i(t)\right) - 41(i_2);$$

$$i2corr' = \left(\frac{|i_{4.1}| + b'|i_5| - c|i_{1.1}|}{|i_{4.1}| + b'|i_5|}\right)i_R$$

where:
- a', b', c, d, p', zgr' include manufacturing parameters;
- $i_{4.1}$ includes the current measured during application of the third voltage and approximately 4.1 seconds after initiation of the test sequence;
- $i_5$ includes the current measured during application of the third voltage and approximately 5 seconds after initiation of the test sequence;
- $i_{1.1}$ includes the current measured during application of the second voltage and approximately 1.1 seconds after initiation of the test sequence; and
- $i_2$ includes the current measured during application of the second voltage and approximately 2 seconds after initiation of the test sequence.

In another aspect, a method of determining blood glucose concentration with a glucose measurement system that includes a test strip and test meter is provided. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; applying a first voltage; causing a transformation of analytes in the sample from one form to a different form with reagent in the test chamber; switching the first voltage to a second voltage different than the first voltage; changing the second voltage to a third voltage different from the second voltage; measuring a second current output of the current transient from the electrodes after the changing from the second voltage to the third voltage; estimating approximate steady state current output of the current transient after the third voltage is maintained at the electrodes; calculating a blood glucose concentration.

In yet a further embodiment, a method of determining blood glucose concentration with a glucose measurement system that includes a test strip and test meter is provided. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; applying a first voltage; causing a transformation of analytes in the sample from one form to a different form with reagent in the test chamber; switching the first voltage to a second voltage different than the first voltage; changing the second voltage to a third voltage different from the second voltage; measuring a second current output of the current transient from the electrodes after the changing from the second voltage to the third voltage; estimating approximate steady state current output of the current transient after the third voltage is maintained at the electrodes; calculating a blood glucose concentration based on the first current, second current and third current output of the current transient; deriving a first corrected blood glucose concentration; and deriving a second corrected blood glucose concentration. The third voltage may be different in the magnitude of the electromotive force, in polarity, or combinations of both.

In a further embodiment, a method of determining a hematocrit compensation factor with a glucose measurement system that includes a test strip and test meter is provided. The test meter has a microcontroller configured to apply a plurality of test voltages to the test strip and measure a current transient output resulting from an electrochemical reaction in a test chamber of the test strip. The method can be achieved by: initiating a test sequence after deposition of a sample; applying a first voltage; causing a transformation of analytes in the sample from one form to a different form by application of a plurality of voltages to the sample with reagent in the test chamber; measuring a plurality of current outputs from the test chamber; deriving an initial glucose proportional current based on the plurality of measured current outputs; and formulating a hematocrit compensation factor based on the derived initial glucose proportional current. In this method, the formulating may include dividing the derived initial glucose proportional current by an integration of current measured during application of a second voltage. The integration may include an offset to the integration based on a measured current during application of a second voltage. The method may include the step of calculating a glucose concentration based on a compensation of the derived initial glucose proportional current with the hematocrit compensation factor. Specifically, the hematocrit compensation factor may be of the form:

$$\left(\frac{|i2corr'|}{|i'_L|}\right)^{p'}$$

where p' includes a coefficient and $$i'_L = \left(\sum_{t=1.4\,sec\,s}^{t=4\,sec\,s} i(t)\right) - 41(i_2)$$

where $i_2$ includes a current measured at about 2 seconds after initiation of the test sequence and $41i_2$ includes the offset. In this method, the calculating may utilize an equation of the form:

$$G_1 = \left(\frac{|i2corr'|}{|i'_L|}\right)^{'p}(a'|i2corr'| - zgr') + d;$$

where: $G_1$ includes a glucose concentration;

$$i_r = \sum_{t=4.4}^{t=5} i(t);$$

$$i'_L = \left(\sum_{t\sim1.4\,sec\,s}^{t\sim4\,sec\,s} i(t)\right) - 41(i_2);$$

$$i2corr' = \left(\frac{|i_{4.1}| + b'|i_5| - c|i_{1.1}|}{|i_{4.1}| + b'|i_5|}\right)i_R$$

where:
a', b', c, d, p', zgr' include manufacturing parameters;
$i_{4.1}$ includes the current measured during application of a third voltage and approximately 4.1 seconds after initiation of a test sequence;
$i_5$ includes the current measured during application of the third voltage and approximately 5 seconds after initiation of the test sequence;
$i_{1.1}$ includes the current measured during application of a second voltage and approximately 1.1 seconds after initiation of the test sequence; and
$i_2$ includes the current measured during application of a second voltage and approximately 2 seconds after initiation of the test sequence.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 1C illustrates a perspective view of an assembled test strip suitable for use in the system and methods disclosed herein;

FIG. 1D illustrates an exploded perspective view of an unassembled test strip suitable for use in the system and methods disclosed herein;

FIG. 1E illustrates an expanded perspective view of a proximal portion of the test strip suitable for use in the system and methods disclosed herein;

FIG. 2 illustrates a bottom plan view of one embodiment of a test strip disclosed herein;

FIG. 3 illustrates a side plan view of the test strip of FIG. 2;

FIG. 4A illustrates a top plan view of the test strip of FIG. 3;

FIG. 4B illustrates a partial side view of a proximal portion of the test strip of FIG. 4A;

FIG. 9C illustrates Table HA that shows the various bias levels at different referential glucose datum (nominal values of 65 mg/dL; 240 mg/dL; 450 mg/dL) using the existing Verio technique;

FIG. 9D illustrates Table IIB that shows improvement in bias levels at the same referential datum as in Table IIA by usage of the new technique;

FIG. 11A are plots of the glucose concentration determined by the existing Verio system at various bias levels at each hematocrit level out of 19%; 30%; 40% and 50%;

FIG. 11B are plots of the glucose concentration determined by the new technique at various bias levels at each hematocrit level out of 19%; 30%; 40% and 50%;

FIG. 12A illustrates Table IIIA that shows the various bias levels at different referential glucose datum (65 mg/dL; 240 mg/dL; 450 mg/dL (nominal values)) using the existing Verio technique;

FIG. 12B illustrates Table IIIB that shows the various bias levels at different referential glucose datum (65 mg/dL; 240 mg/dL; 450 mg/dL (nominal values)) using the new technique.

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1A:
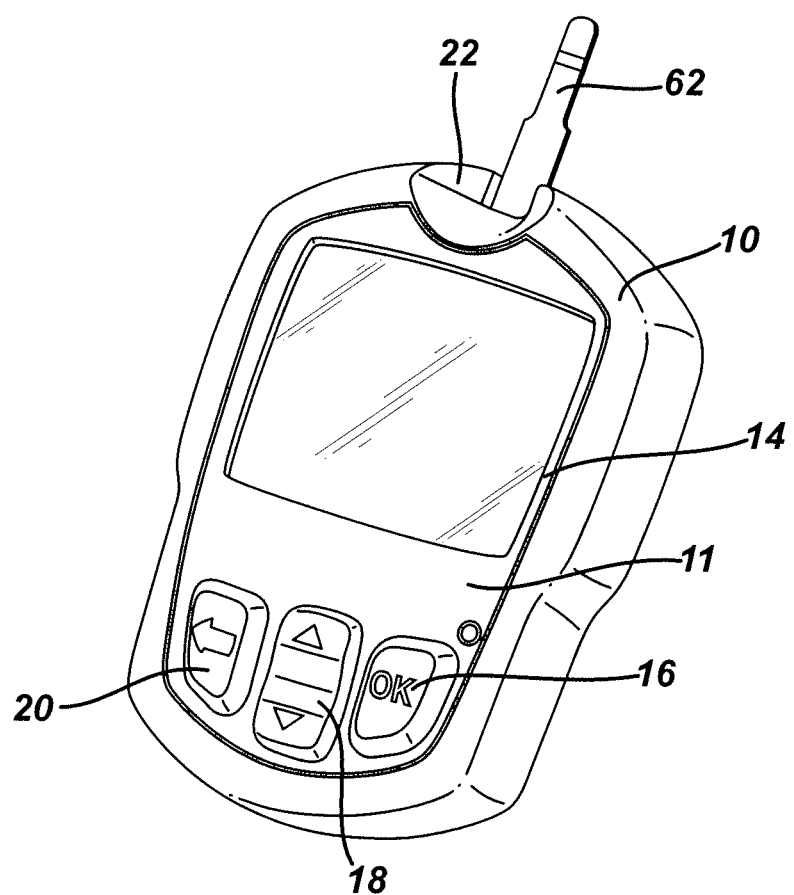
FIG. 1A illustrates a preferred blood glucose measurement system.

FIG. 1A illustrates a diabetes management system that includes a meter 10 and a biosensor in the form of a glucose test strip 62. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Referring back to FIG. 1A, glucose meter or meter unit 10 may include a housing 11, user interface buttons (16, 18, and 20), a display 14, and a strip port opening 22. User interface buttons (16, 18, and 20) may be configured to allow the entry of data, navigation of menus, and execution of commands. User interface button 18 may be in the form of a two way toggle switch. Data may include values representative of analyte concentration, and/or information, which are related to the everyday lifestyle of an individual. Information, which is related to the everyday lifestyle, may include food intake, medication use, occurrence of health check-ups, and general health condition and exercise levels of an individual. The electronic components of meter 10 may be disposed on a circuit board 34 that is within housing 11.

Figure 1B:
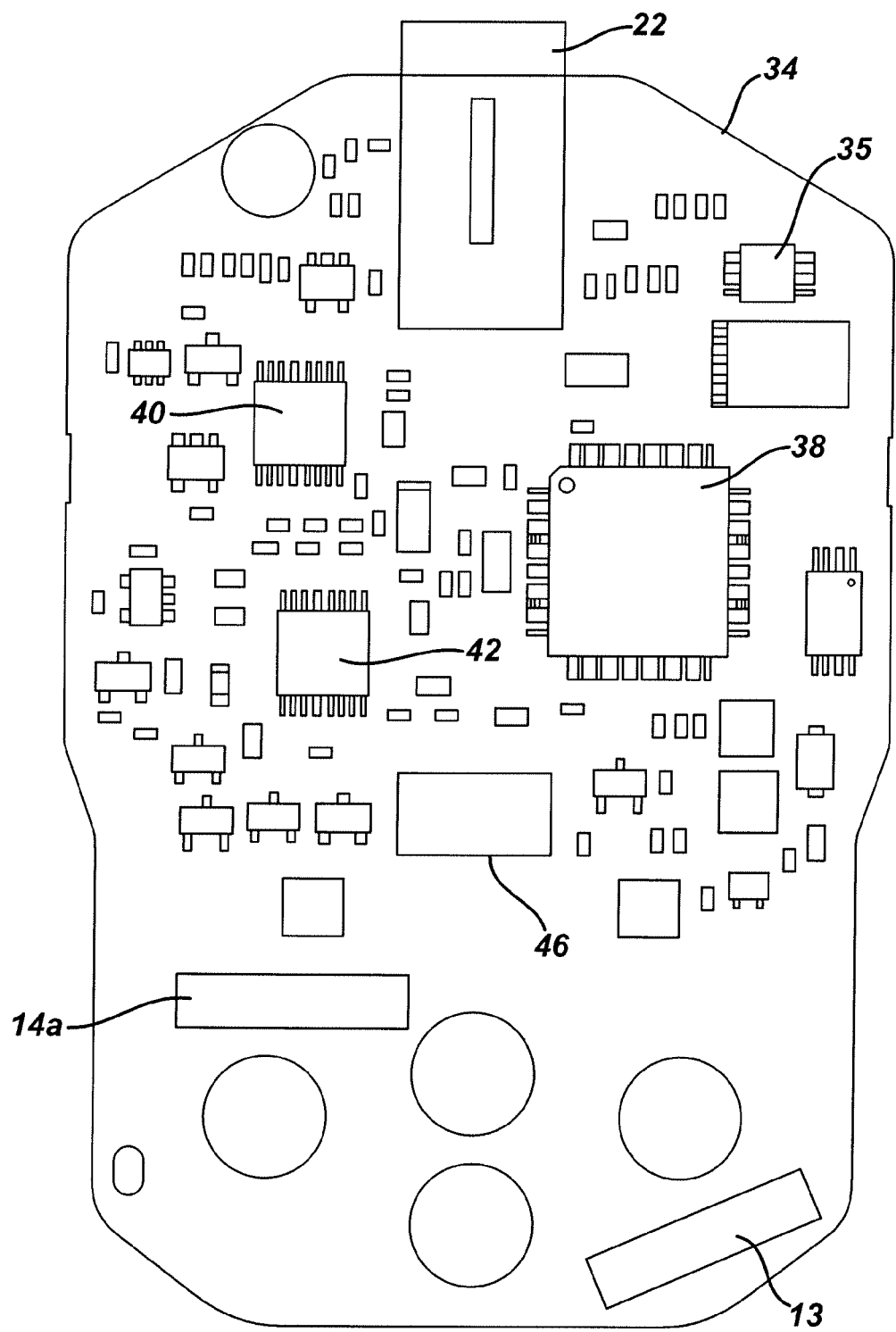
FIG. 1B illustrates the various components disposed in the meter of FIG. 1A.

FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 may include two or more operational amplifiers configured to provide a portion of the potentiostat function and the current measurement function. The potentiostat function may refer to the application of a test voltage between at least two electrodes of a test strip. The current function may refer to the measurement of a test current resulting from the applied test voltage. The current measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14a may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured to keep current time related to the geographic region in which the user is located and also for measuring time. The meter unit may be configured to be electrically connected to a power supply such as, for example, a battery.

FIGS. 1C-1E, 2, 3, and 4B show various views of an exemplary test strip 62 suitable for use with the methods and systems described herein. In an exemplary embodiment, a test strip 62 is provided which includes an elongate body extending from a distal end 80 to a proximal end 82, and having lateral edges 56, 58, as illustrated in FIG. 1C. As shown in FIG. 1D, the test strip 62 also includes a first electrode layer 66, a second electrode layer 64, and a spacer 60 sandwiched in between the two electrode layers 64 and 66. The first electrode layer 66 may include a first electrode 66, a first connection track 76, and a first contact pad 67, where the first connection track 76 electrically connects the first electrode 66 to the first contact pad 67, as shown in FIGS. 1D and 4B. Note that the first electrode 66 is a portion of the first electrode layer 66 that is immediately underneath the reagent layer 72, as indicated by FIGS. 1D and 4B. Similarly, the second electrode layer 64 may include a second electrode 64, a second connection track 78, and a second contact pad 63, where the second connection track 78 electrically connects the second electrode 64 with the second contact pad 63, as shown in FIGS. 1D, 2, and 4B. Note that the second electrode 64 is a portion of the second electrode layer 64 that is above the reagent layer 72, as indicated by FIG. 4B.

As shown, the sample-receiving chamber 61 is defined by the first electrode 66, the second electrode 64, and the spacer 60 near the distal end 80 of the test strip 62, as shown in FIGS. 1D and 4B. The first electrode 66 and the second electrode 64 may define the bottom and the top of sample-receiving chamber 61, respectively, as illustrated in FIG. 4B. A cutout area 68 of the spacer 60 may define the sidewalls of the sample-receiving chamber 61, as illustrated in FIG. 4B. In one aspect, the sample-receiving chamber 61 may include ports 70 that provide a sample inlet and/or a vent, as shown in FIGS. 1C to 1E. For example, one of the ports may allow a fluid sample to ingress and the other port may allow air to egress.

In an exemplary embodiment, the sample-receiving chamber 61 (or test cell or test chamber) may have a small volume. For example, the chamber 61 may have a volume in the range of from about 0.1 microliters to about 5 microliters, about 0.2 microliters to about 3 microliters, or, preferably, about 0.3 microliters to about 1 microliter. To provide the small sample volume, the cutout 68 may have an area ranging from about 0.01 cm$^2$ to about 0.2 cm$^2$, about 0.02 cm$^2$ to about 0.15 cm$^2$, or, preferably, about 0.03 cm$^2$ to about 0.08 cm$^2$. In addition, first electrode 66 and second electrode 64 may be spaced apart in the range of about 1 micron to about 500 microns, preferably between about 10 microns and about 400 microns, and more preferably between about 40 microns and about 200 microns. The relatively close spacing of the electrodes may also allow redox cycling to occur, where oxidized mediator generated at first electrode 66, may diffuse to second electrode 64 to become reduced, and subsequently diffuse back to first electrode 66 to become oxidized again. Those skilled in the art will appreciate that various such volumes, areas, and/or spacing of electrodes is within the spirit and scope of the present disclosure.

In one embodiment, the first electrode layer 66 and the second electrode layer 64 may be a conductive material formed from materials such as gold, palladium, carbon, silver, platinum, tin oxide, iridium, indium, or combinations thereof (e.g., indium doped tin oxide). In addition, the electrodes may be formed by disposing a conductive material onto an insulating sheet (not shown) by a sputtering, electroless plating, or a screen-printing process. In one exemplary embodiment, the first electrode layer 66 and the second electrode layer 64 may be made from sputtered palladium and sputtered gold, respectively. Suitable materials that may be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated. Applicants note that various other materials for the first electrode layer 66, the second electrode layer 64, and/or the spacer 60 are within the spirit and scope of the present disclosure.

Either the first electrode 66 or the second electrode 64 may perform the function of a working electrode depending on the magnitude and/or polarity of the applied test voltage. The working electrode may measure a limiting test current that is proportional to the reduced mediator concentration. For example, if the current limiting species is a reduced mediator (e.g., ferrocyanide), then it may be oxidized at the first electrode 66 as long as the test voltage is sufficiently greater than the redox mediator potential with respect to the second electrode 64. In such a situation, the first electrode 66 performs the function of the working electrode and the second electrode 64 performs the function of a counter/reference electrode. Applicants note that one may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term "bulk solution" refers to a portion of the solution sufficiently far away from the working electrode where the reduced mediator is not located within a depletion zone. It should be noted that unless otherwise stated for test strip 62, all potentials applied by test meter 10 will hereinafter be stated with respect to second electrode 64.

Similarly, if the test voltage is sufficiently less than the redox mediator potential, then the reduced mediator may be oxidized at the second electrode 64 as a limiting current. In such a situation, the second electrode 64 performs the function of the working electrode and the first electrode 66 performs the function of the counter/reference electrode.

Initially, an analysis may include introducing a quantity of a fluid sample into a sample-receiving chamber 61 via a port 70. In one aspect, the port 70 and/or the sample-receiving chamber 61 may be configured such that capillary action causes the fluid sample to fill the sample-receiving chamber 61. The first electrode 66 and/or second electrode 64 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode and/or the second electrode.

In the analysis of strip 62 above, reagent layer 72 can include glucose dehydrogenase (GDH) based on the PQQ co-factor and ferricyanide. In another embodiment, the enzyme GDH based on the PQQ co-factor may be replaced with the enzyme GDH based on the FAD co-factor. When blood or control solution is dosed into a sample reaction chamber 61, glucose is oxidized by $GDH_{(ox)}$ and in the process converts $GDH_{(ox)}$ to $GDH_{(red)}$, as shown in the chemical transformation T.1 below. Note that $GDH_{(ox)}$ refers to the oxidized state of GDH, and $GDH_{(red)}$ refers to the reduced state of GDH.

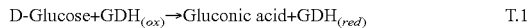

$$\text{D-Glucose} + GDH_{(ox)} \rightarrow \text{Gluconic acid} + GDH_{(red)} \qquad \text{T.1}$$

Next, $GDH_{(red)}$ is regenerated back to its active oxidized state by ferricyanide (i.e. oxidized mediator or $Fe(CN)_6^{3-}$) as shown in chemical transformation T.2 below. In the process of regenerating $GDH_{(ox)}$, ferrocyanide (i.e. reduced mediator or $Fe(CN)_6^{4-}$) is generated from the reaction as shown in T.2:

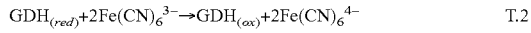

$$GDH_{(red)} + 2Fe(CN)_6^{3-} \rightarrow GDH_{(ox)} + 2Fe(CN)_6^{4-} \qquad \text{T.2}$$

Figure 5:
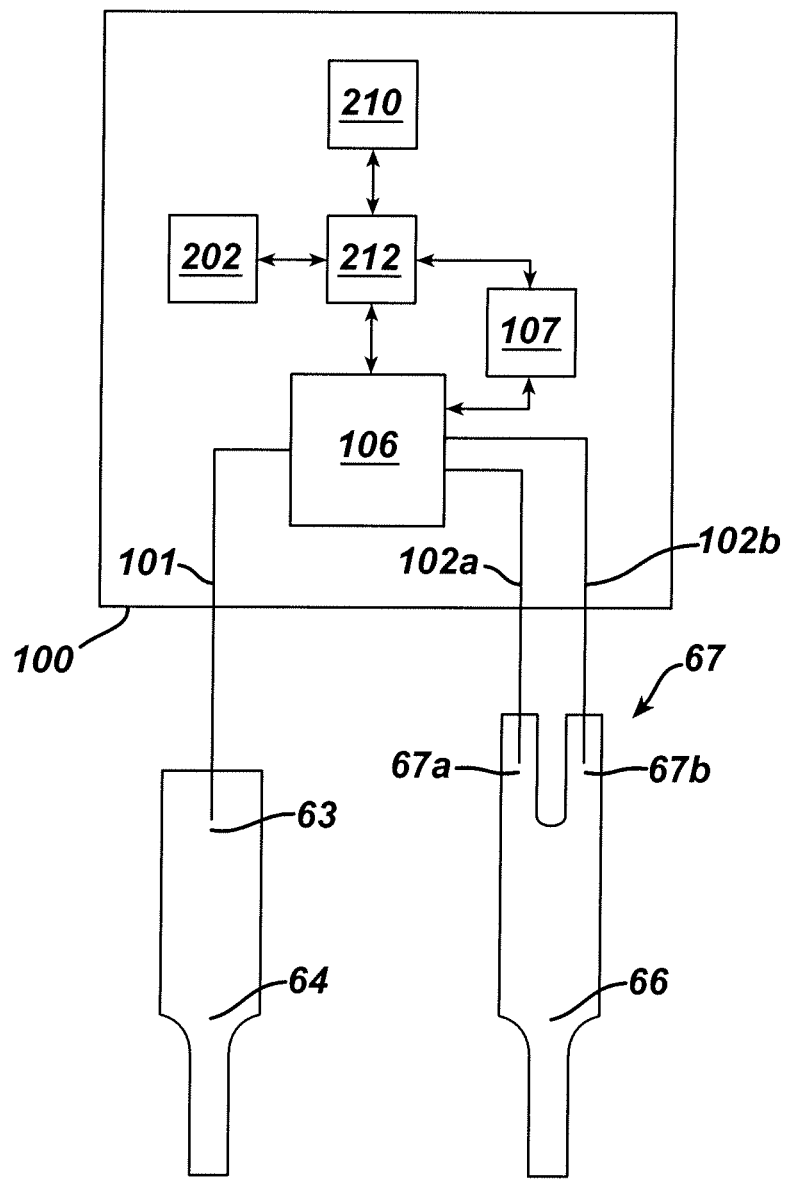
FIG. 5 illustrates a simplified schematic showing a test meter electrically interfacing with portions of a test strip disclosed herein.

FIG. 5 provides a simplified schematic showing a test meter 100 interfacing with a first contact pad 67a, 67b and a second contact pad 63. The second contact pad 63 may be used to establish an electrical connection to the test meter through a U-shaped notch 65, as illustrated in FIG. 2. In one embodiment, the test meter 100 may include a second electrode connector 101, and a first electrode connectors (102a, 102b), a test voltage unit 106, a current measurement unit 107, a processor 212, a memory unit 210, and a visual display 202, as shown in FIG. 5. The first contact pad 67 may include two prongs denoted as 67a and 67b. In one exemplary embodiment, the first electrode connectors 102a and 102b separately connect to prongs 67a and 67b, respectively. The second electrode connector 101 may connect to second contact pad 63. The test meter 100 may measure the resistance or electrical continuity between the prongs 67a and 67b to determine whether the test strip 62 is electrically connected to the test meter 10.

In one embodiment, the test meter 100 may apply a test voltage and/or a current between the first contact pad 67 and the second contact pad 63. Once the test meter 100 recognizes that the strip 62 has been inserted, the test meter 100 turns on and initiates a fluid detection mode. In one embodiment, the fluid detection mode causes test meter 100 to apply a constant current of about 1 microampere between the first electrode 66 and the second electrode 64. Because the test strip 62 is initially dry, the test meter 10 measures a relatively large voltage. When the fluid sample bridges the gap between the first electrode 66 and the second electrode 64 during the dosing process, the test meter 100 will measure a decrease in measured voltage that is below a predetermined threshold causing test meter 10 to automatically initiate the glucose test.

Figure 6:
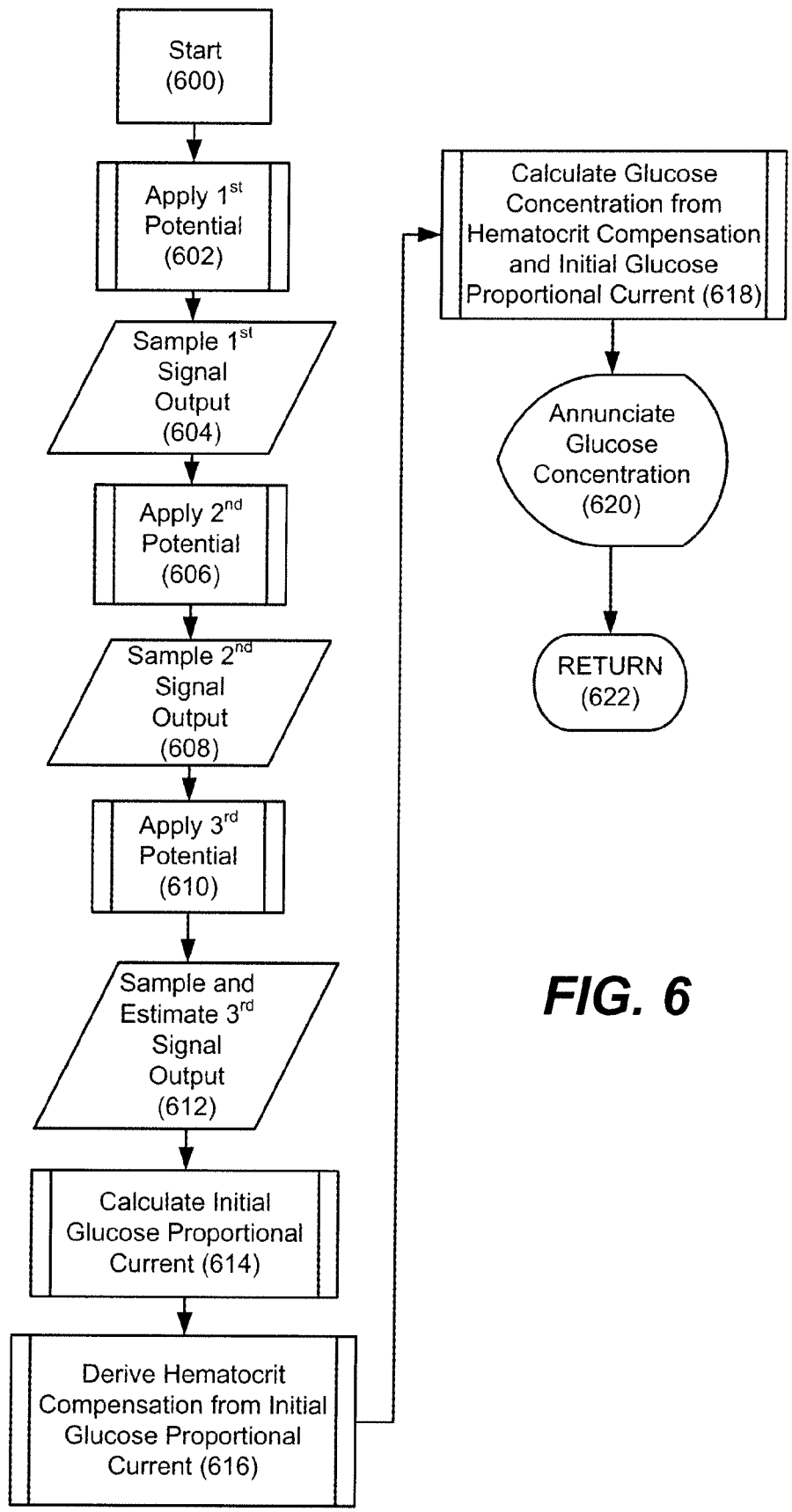
FIG. 6 illustrates generally the steps involved in determining the glucose measurement.

Referring to FIG. 6, a method 600 for determining an interferent-corrected analyte concentration (e.g., glucose) that uses the aforementioned meter 10 and test strip 62 embodiments will now be described. In the method, meter 10 and test strip 62 are provided. Meter 10 may include electronic circuitry that can be used to apply a plurality of voltages to the test strip 62 and to measure a current transient output resulting from an electrochemical reaction in a test chamber of the test strip 62. Meter 10 also may include a signal processor with a set of instructions for the method of determining an analyte concentration in a fluid sample as disclosed herein. In one embodiment, the analyte is blood glucose.

Figure 7A:
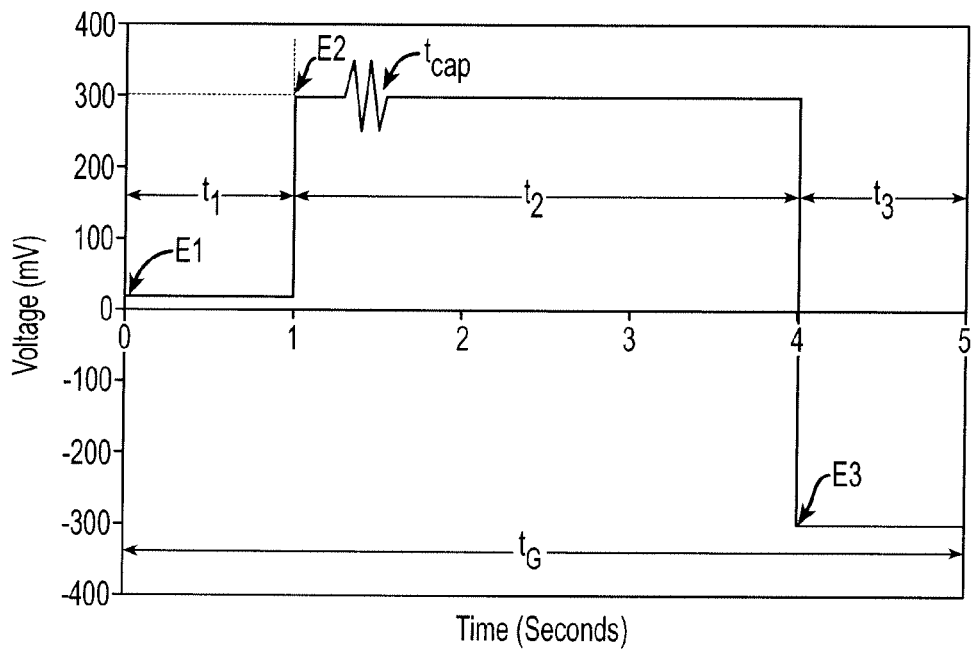
FIG. 7A shows an example of a tri-pulse potential waveform applied by the test meter of FIG. 5 to the working and counter electrodes for prescribed time intervals.

FIG. 7A is an exemplary chart of a plurality of test voltages applied to the test strip 62 for prescribed intervals. The plurality of test voltages may include a first test voltage E1 for a first time interval $t_1$, a second test voltage E2 for a second time interval $t_2$, and a third test voltage E3 for a third time interval $t_3$. The third voltage E3 may be different in the magnitude of the electromotive force, in polarity, or combinations of both with respect to the second test voltage E2. In the preferred embodiments, E3 may be of the same magnitude as E2 but opposite in polarity. A glucose test time interval $t_G$ represents an amount of time to perform the glucose test (but not necessarily all the calculations associated with the glucose test). Glucose test time interval $t_G$ may range from about 1.1 seconds to about 5 seconds. Further, as illustrated in FIG. 6A, the second test voltage E2 may include a constant (DC) test voltage component and a superimposed alternating (AC), or alternatively oscillating, test voltage component. The superimposed alternating or oscillating test voltage component may be applied for a time interval indicated by $t_{cap}$.

The plurality of test current values measured during any of the time intervals may be performed at a frequency ranging from about 1 measurement per microsecond to about one measurement per 100 milliseconds and preferably at about 50 milliseconds. While an embodiment using three test voltages in a serial manner is described, the glucose test may include different numbers of open-circuit and test voltages. For example, as an alternative embodiment, the glucose test could include an open-circuit for a first time interval, a second test voltage for a second time interval, and a third test voltage for a third time interval. It should be noted that the reference to "first," "second," and "third" are chosen for convenience and do not necessarily reflect the order in which the test voltages are applied. For instance, an embodiment may have a potential waveform where the third test voltage may be applied before the application of the first and second test voltage.

In exemplary step 600, the glucose assay is initiated by inserting a test strip 62 into the test meter 10 and by depositing a sample on the test strip 62. In exemplary step 602, the test meter 10 may apply a first test voltage E1 (e.g., approximately 20 mV in FIG. 7A) between first electrode 66 and second electrode 64 for a first time interval $t_1$ (e.g., 1 second in FIG. 7A). The first time interval $t_1$ may range from about 0.1 seconds to about 3 seconds and preferably range from about 0.2 seconds to about 2 seconds, and most preferably range from about 0.3 seconds to about 1.1 seconds.

Figure 7B:
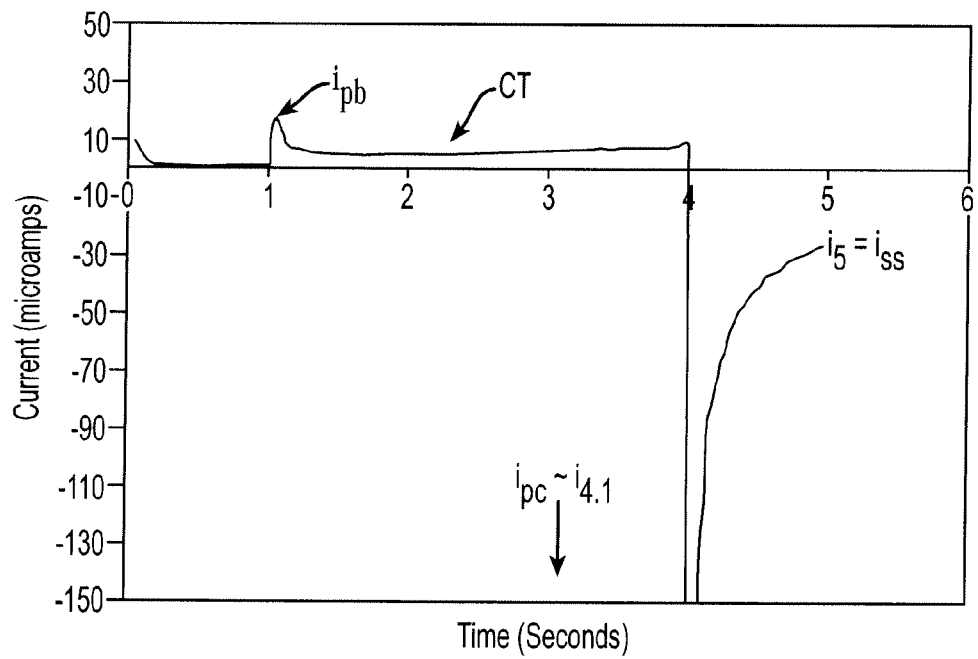
FIG. 7B shows a first and second current transient CT generated testing a physiological sample.

The first time interval $t_1$ may be sufficiently long so that the sample-receiving chamber 61 may fully fill with sample and also so that the reagent layer 72 may at least partially dissolve or solvate. In one aspect, the first test voltage E1 may be a value relatively close to the redox potential of the mediator so that a relatively small amount of a reduction or oxidation current is measured. FIG. 7B shows that a relatively small amount of current is observed during the first time interval $t_1$ compared to the second and third time intervals $t_2$ and $t_3$. For example, when using ferricyanide and/or ferrocyanide as the mediator, the first test voltage E1 in FIG. 7A may range from about 1 mV to about 100 mV, preferably range from about 5 mV to about 50 mV, and most preferably range from about 10 mV to about 30 mV. Although the applied voltages are given as positive values in the preferred embodiments, the same voltages in the negative domain could also be utilized to accomplish the intended purpose of the claimed invention. During this interval, the first current output may be sampled by the processor to collect current values over this interval in step 604.

In exemplary step 606, after applying the first test voltage E1 (step 602) and sampling the output (step 604), the test meter 10 applies a second test voltage E2 between first electrode 66 and second electrode 64 (e.g., approximately 300 mVolts in FIG. 7A), for a second time interval $t_2$ (e.g., about 3 seconds in FIG. 7A). The second test voltage E2 may be a value different than the first test voltage E1 and may be sufficiently negative of the mediator redox potential so that a limiting oxidation current is measured at the second electrode 64. For example, when using ferricyanide and/or ferrocyanide as the mediator, the second test voltage E2 may range from about zero mV to about 600 mV, preferably range from about 100 mV to about 600 mV, and more preferably is about 300 mV.

The second time interval $t_2$ should be sufficiently long so that the rate of generation of reduced mediator (e.g., ferrocyanide) may be monitored based on the magnitude of a limiting oxidation current. Reduced mediator is generated by enzymatic reactions with the reagent layer 72. During the second time interval $t_2$, a limiting amount of reduced mediator is oxidized at second electrode 64 and a non-limiting amount of oxidized mediator is reduced at first electrode 66 to form a concentration gradient between first electrode 66 and second electrode 64.

In an exemplary embodiment, the second time interval $t_2$ should also be sufficiently long so that a sufficient amount of ferricyanide may be diffused to the second electrode 64 or diffused from the reagent on the first electrode. A sufficient amount of ferricyanide is required at the second electrode 64 so that a limiting current may be measured for oxidizing ferrocyanide at the first electrode 66 during the third test voltage E3. The second time interval $t_2$ may be less than about 60 seconds, and preferably may range from about 1.1 seconds to about 10 seconds, and more preferably range from about 2 seconds to about 5 seconds. Likewise, the time interval indicated as $t_{cap}$ in FIG. 7A may also last over a range of times, but in one exemplary embodiment it has a duration of about 20 milliseconds. In one exemplary embodiment, the superimposed alternating test voltage component is applied after about 0.3 seconds to about 0.4 seconds after the application of the second test voltage E2, and induces a sine wave having a frequency of about 109 Hz with an amplitude of about +/−50 mV. During this interval, a second current output may be sampled by the processor to collect current values over this interval in step 608.

FIG. 7B shows a relatively small peak $i_{pb}$ after the beginning of the second time interval $t_2$ followed by a gradual increase of an absolute value of an oxidation current during the second time interval $t_2$. The small peak $i_{pb}$ occurs due oxidation of endogenous or exogenous reducing agents (e.g., uric acid) after a transition from first voltage E1 to second voltage E2. Thereafter, there is a gradual absolute decrease in oxidation current after the small peak $i_{pb}$ is caused by the generation of ferrocyanide by reagent layer 72, which then diffuses to second electrode 64.

In exemplary step 610, after applying the second test voltage E2 (step 606) and sampling the output (step 608), the test meter 10 applies a third test voltage E3 between the first electrode 66 and the second electrode 64 (e.g., about −300 mVolts in FIG. 7A) for a third time interval $t_3$ (e.g., 1 second in FIG. 7A). The third test voltage E3 may be a value sufficiently positive of the mediator redox potential so that a limiting oxidation current is measured at the first electrode 66. For example, when using ferricyanide and/or ferrocyanide as the mediator, the third test voltage E3 may range from about zero mV to about −600 mV, preferably range from about −100 mV to about −600 mV, and more preferably is about −300 mV.

The third time interval $t_3$ may be sufficiently long to monitor the diffusion of reduced mediator (e.g., ferrocyanide) near the first electrode 66 based on the magnitude of the oxidation current. During the third time interval $t_3$, a limiting amount of reduced mediator is oxidized at first electrode 66 and a non-limiting amount of oxidized mediator is reduced at the second electrode 64. The third time interval $t_3$ may range from about 0.1 seconds to about 5 seconds and preferably range from about 0.3 seconds to about 3 seconds, and more preferably range from about 0.5 seconds to about 2 seconds.

FIG. 7B shows a relatively large peak $i_{pc}$ at the beginning of the third time interval $t_3$ followed by a decrease to a steady-state current $i_{ss}$ value. In one embodiment, the second test voltage E2 may have a first polarity and the third test voltage E3 may have a second polarity that is opposite to the first polarity. In another embodiment, the second test voltage E2 may be sufficiently negative of the mediator redox potential and the third test voltage E3 may be sufficiently positive of the mediator redox potential. The third test voltage E3 may be applied immediately after the second test voltage E2. However, one skilled in the art will appreciate that the magnitude and polarity of the second and third test voltages may be chosen depending on the manner in which analyte concentration is determined.

Hereafter, applicant describes the glucose concentration determination for the embodiments described herein. FIGS. 7A and 7B show the sequence of events in the Verio test strip transient. At approximately 1.1 second after initiation of the test sequence (and shortly after making the second electrode layer (64) electrode the working electrode due to application of the second voltage E2), when no reagent has yet reached the first electrode, and current is due presumably to only interfering reducing agents in plasma (in the absence of mediator), a current measurement is taken to later correct for interferences. Between about 1.4 seconds and about 4 seconds, when (at least in the latter part of this interval when a second voltage E2 is applied) mediator and oxidized mediator have been able to diffuse to the second electrode, a first glucose-proportional current, $i_l$, is measured. Shortly after making the first electrode the working electrode via application of the third voltage E3, 2 single-point measurements (at approximately 4.1 and 5 second) and one integrated measurement $i_r$ are taken. The measurements sampled respectively at 1.1, 4.1 and 5 seconds are used to correct $i_r$ for additive current from interfering reducing agents (i2corr). The ratio of $i_l$ to $i_r$ is used to correct i2corr for the effects of hematocrit.

The strategy employed in improving the existing glucose calculation was to find ways to make the two functions, initial glucose function i2corr and hematocrit compensation function:

$$\left(\frac{i_R}{i_L}\right)^p \tag{7.6}$$

separately independent of levels of interfering reducing agent. The strategy is devised in two parts, as described below.

Data for Technique Development and Demonstration of Performance with Improved Technique Data from two studies was used for both analysis of the problems with the current Verio technique and the relative performance of revised technique functions. The first data set was data from a uric acid spiking study. This involved 3 (hematocrit unadjusted) bloods and a total of 7 Verio strip lots, with spiking levels ranging from 0-24 mg/dl uric acid (basis whole blood). Glucose levels were 65, 240 and 450 mg/dl. The second data set[1] was a hematocrit study with 4 lots, 3 blood donors (unadjusted uric acid), 5 glucose levels (30, 65, 240, 450 and 560 mg/dl), and 5 hematocrit levels (19, 30, 40, 50 and 61%).

Initial Glucose i2corr Derivation.

Equation 7 above would only work correctly if $$i_{4.1} + bi_5 = 2i_{1.1} \quad (8)$$

when glucose=0.

Or, put another way:

$$\left(\frac{d[i_{4.1} + bi_5]}{d_{1.1}}\right)_{glucose=0} = 2 \quad (9)$$

This would cause i2corr to go to 0 when glucose=0, or to iR when $i(1.1)=0$. This follows from a mechanism in which $i(1.1)$ represents current from non-glucose interfering reducing agents, and $i(4.1)$ and $i(5)$ contain current components due to both glucose and reducing agents. Furthermore, the contributions to $i(4.1)$ and $i(5)$ from interfering reducing agents are both proportional to $i(1.1)$, and the glucose-dependent currents contained in $(4.1)$ and $i(5)$ are both proportional to glucose. According to this scheme, if b is correctly determined, i2corr represents the portion of iR that is due solely to glucose.

Figure 8:
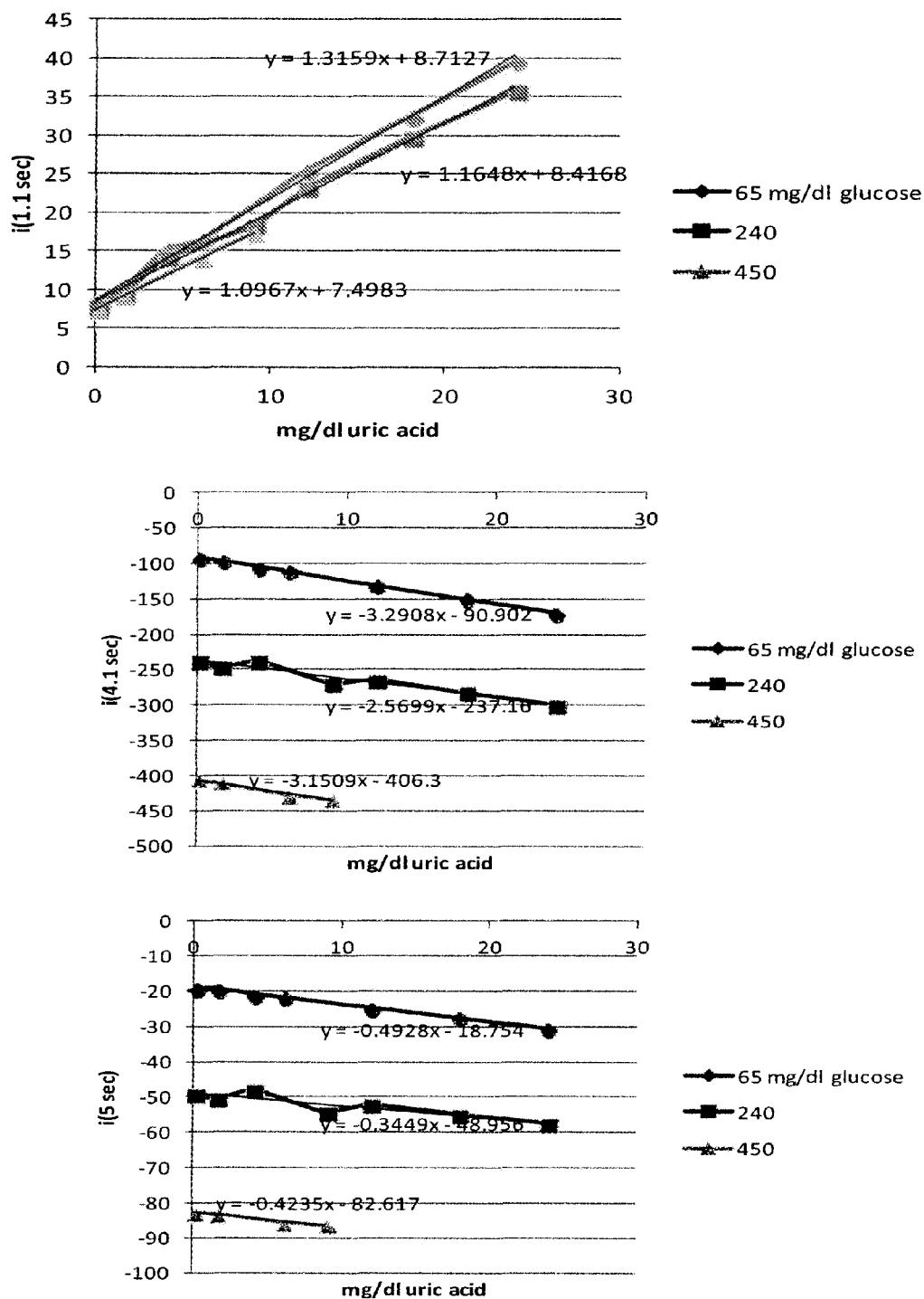
FIG. 8 are plots of the glucose concentration G1 at the referential datum of 65 mg/dL; 240 mg/dL; and 450 mg/dL versus concentration calculated by the existing Verio system at various levels of uric acid in the measured samples.

FIG. 8 shows the averaged currents from the uric acid spiking study. The slopes of current vs. uric acid spiking level are shown in Table I.

TABLE I

Slopes of Averaged Currents (Absolute Value)

| Glucose Conc. | $di_{1.1}/dUA$ | $di_{4.1}/dUA$ | $di_5/dUA$ | $di_5/di4.1$ | $di_{1.1}/di_{4.1}$ |
|---|---|---|---|---|---|
| 64 mg/dL | 1.1316 | 3.290 | 0.493 | 0.15 | 0.4 |
| 240 | 1.165 | 2.570 | 0.345 | 0.134 | 0.453 |
| 450 | 1.097 | 3.15 | 0.424 | 0.135 | 0.348 |
| avg | 1.193 | 3.003 | 0.421 | 0.140 | 0.401 |

It can be shown algebraically that if $$ei_{4.1} + bi_5 = ci_{1.1} \quad (10)$$

then $$c = \frac{1 + b\left(\frac{di_5}{di_{4.1}}\right)}{\frac{di_{1.1}}{di_{4.1}}} \quad \text{(for } e = 1\text{)} \quad (11)$$

substituting average values from table I:

$$c = \frac{1 + b(0.14)}{0.401} \quad (11a)$$

solving for c and substituting into Eq. (10):

$$ei_{4.1} + bi_5 = 2.76i_{1.1} \quad (11c)$$

if e is set to 1, Eq. (11c) becomes:

$$1 \cdot i_{4.1} + bi_5 = 2.76i_{1.1} \text{ (for } b = 0.678\text{)} \quad (8b)$$

By comparing Equations (8) (which defines the requirements for correctly functioning values of coefficients in the correction function i2corr) and (8b), it can be seen that i2corr, as currently used in Verio test strip and defined in Eq. (7), under-corrects for interfering substances because the coefficient for $i(1.1)$ is too small by a factor of 2/2.76. This results in the failure to completely compensate for added uric acid at low glucose. At higher glucose levels, the relative magnitudes of the uric acid currents are too small for the error to be noticeable.

If i2corr is expressed as:

$$i2corr = \left(\frac{|i_{4.1}| + b|i_5| - c|i_{1.1}|}{|i_{4.1}| + b|i_5|}\right) i_R \quad (12)$$

Then there are actually an infinite number of coefficients which would work for i2corr, as long as the relationship between b and c is as defined in Eq. (11). If a coefficient, e, not equal to 1, is applied to $i(1.1)$, as in Eq. (11c), then the coefficients b and c would become:

$$b = 0.678e \quad (12.5)$$

$$c = 2.76e \quad (12.6)$$

To further improve the performance of the glucose measurement system, applicant has made modification to Eq. 12 as follow:

$$i2corr' = \left(\frac{|i_{4.1}| + b'|i_5| - c'|i_{1.1}|}{|i_{4.1}| + b'|i_5|}\right) i_R \quad (13)$$

Where b'=4.9 and c'=4.24 are new coefficients for use with the inventor's newly discovered technique.

These coefficients satisfy the conditions just described. According to Equations (11.c), (12.5), and (12.6), other coefficient values would also satisfy these conditions, as follows:

$$i2corr' = \left(\frac{e|i_{4.1}| + 0.678e|i_5| - 2.76e|i_{1.1}|}{|i_{4.1}| + 0.678e|i_5|}\right) i_R$$

where e can have any value.

Hematocrit Compensation Derivation.

Two modifications were made to the hematocrit compensation function $$\left(\frac{i_R}{i_L}\right)^p$$

(Equation 7.6 above) to remove the distorting effect of interfering substance currents of the hematocrit compensation function.

First, the initial glucose function i2corr', was substituted for $i_R$ in Equation 7.6. Secondly, $i_2$ was used to estimate the magnitude of the steady state interferent current underlying $i_L$ and used to correct $i_L$ which is designated as $i_L'$.

Experiments with reducing substances show that at 2 seconds, the decay of the interferent current has just about reached completion. Since $i_L'$ is integrated between 1.4 and 4 seconds, and data sample are taken at 50 msec intervals, it would be assumed that $53*i_2$ would be approximately the value to be subtracted from iL to correct. In practice it was found that $41*i_2$ worked best. Consequently, $i_L'$ has the following form:

$$i_L' = \left(\sum_{t=1.4\,sec\,s}^{t=4\,sec\,s} i(t)\right) - 41(i_2). \quad \text{Eq. 14}$$

This leaves zgr' in Equation (7.5) which is multiplied by the hematocrit compensation factor. If zgr' is considered to be an offset current caused by a contaminant which is dissolved into plasma, such as ferrocyanide already present in the reagent, this makes sense because its diffusion would be affected by red blood cells. But if there is a constant offset current not affected by hematocrit, it would be inappropriate to multiply it by the hematocrit compensation factor. For this reason, a second offset constant d was introduced.

Glucose Concentration Derivation.

Combining both derivations above gives the glucose concentration calculation in Eq. 14.

$$G_1 = \left(\frac{|i2corr'|}{|i_L''|}\right)^{p} (a'|i2corr'| - zgr') + d; \quad (15)$$

where: $G_1$ comprises a glucose concentration;

$$i_r = \sum_{t=4.4}^{t=5} i(t); \quad (16)$$

$$i_l' = \left(\sum_{t=1.4\,sec\,s}^{t=4\,sec\,s} i(t)\right) - 41(i_2); \quad (14)$$

$$i2corr' = \left(\frac{|i_{4.1}| + b'|i_5| - c|i_{1.1}|}{|i_{4.1}| + b'|i_5|}\right) i_r \quad (13)$$

where:
a', b', c, d, p', zgr' are derived manufacturing parameters;
$i_{4.1}$ includes the current measured during application of the third voltage; $i_5$ includes the current measured during application of the third voltage; $i_{1.1}$ includes the current measured during application of the second voltage; and $i_2$ includes the current measured during application of the second voltage.

In Equation 15, the value p' (which is probably insignificantly different from the original p) was determined by least squares fitting of the data from the hematocrit study. The coefficient a' is slightly different from the original coefficient, was determined from the uric acid study data, as were d and zgr'. It is interesting to note that the best fit selected values of zgr' and d that were close in magnitude. Because of the opposite signs, this may be suggesting that in fact no offset is needed.

Demonstration of performance with New Technique.

Figure 9A:
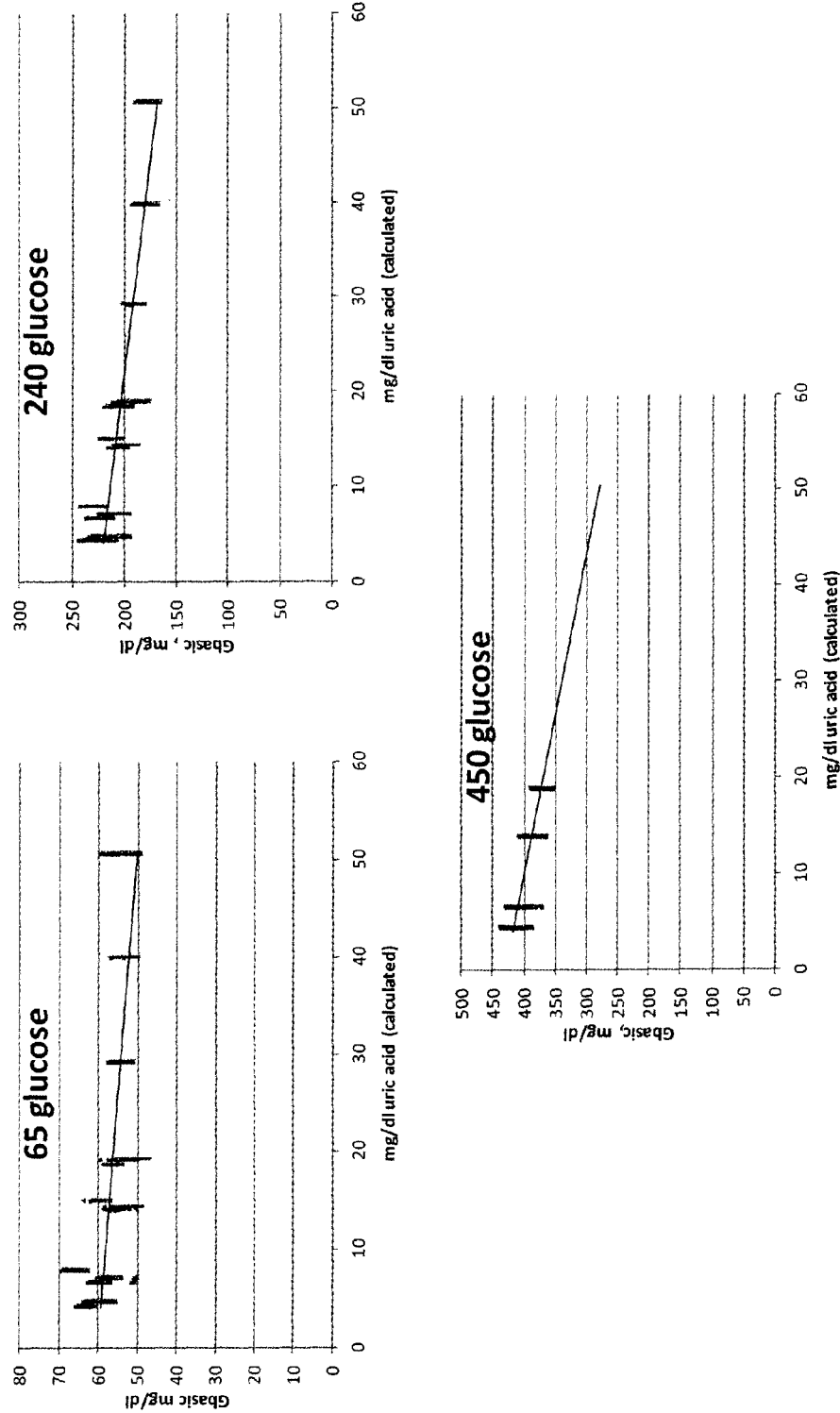
FIG. 9A are plots of the glucose concentration at the same referential datum and uric acid levels as in FIG. 8 but calculated with the existing technique.
Figure 9B:
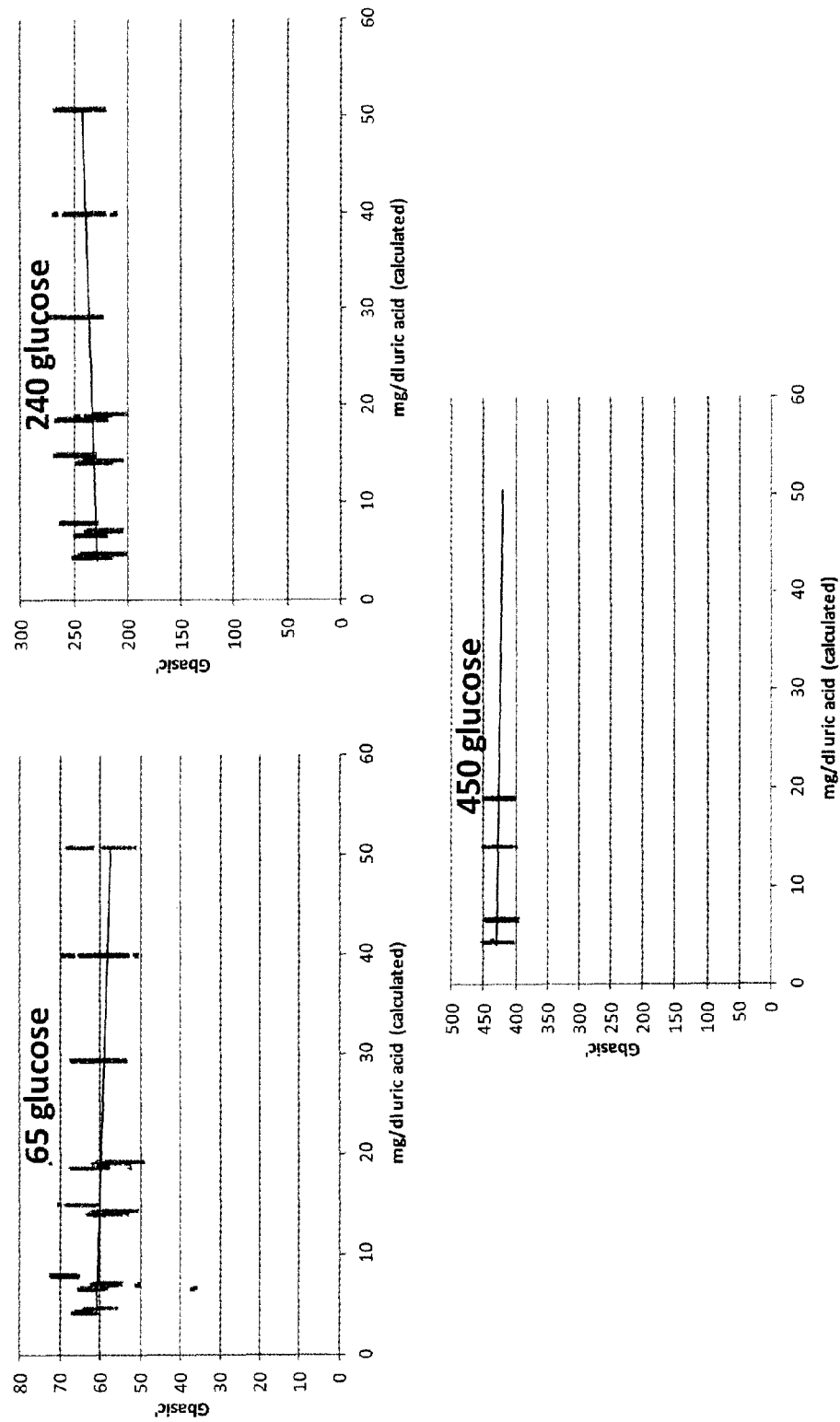
FIG. 9B are plots of the glucose concentration at the same referential datum and uric acid levels as in FIG. 8 but calculated with the new technique invented by applicant.
Figure 10A:
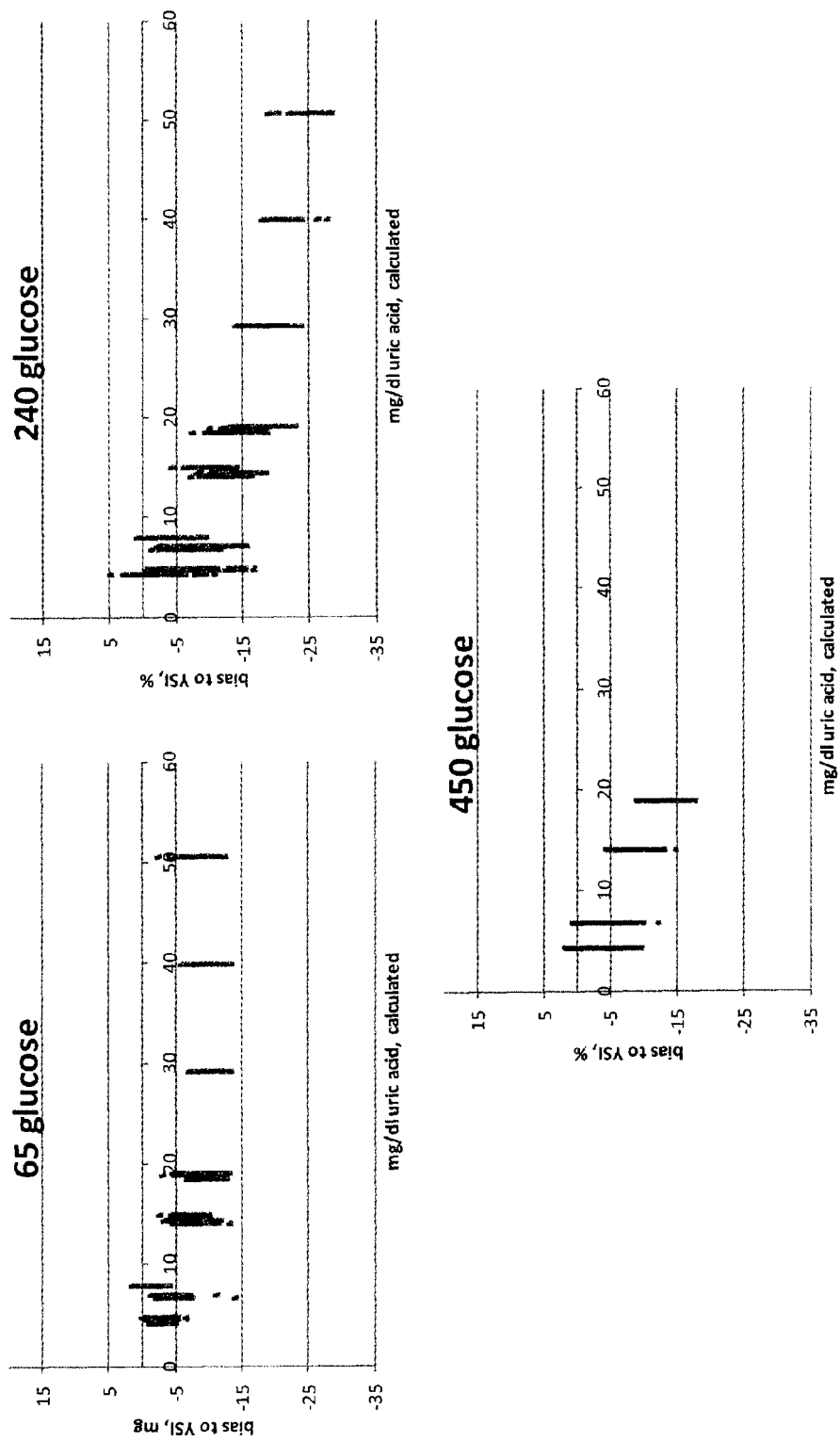
FIG. 10A are plots of the glucose concentration at the referential datum of 65 mg/dL; 240 mg/dL; and 450 mg/dL (nominal values) versus concentration calculated by the existing Verio system and corrected for temperature variations at various levels of uric acid in the measured samples.
Figure 10B:
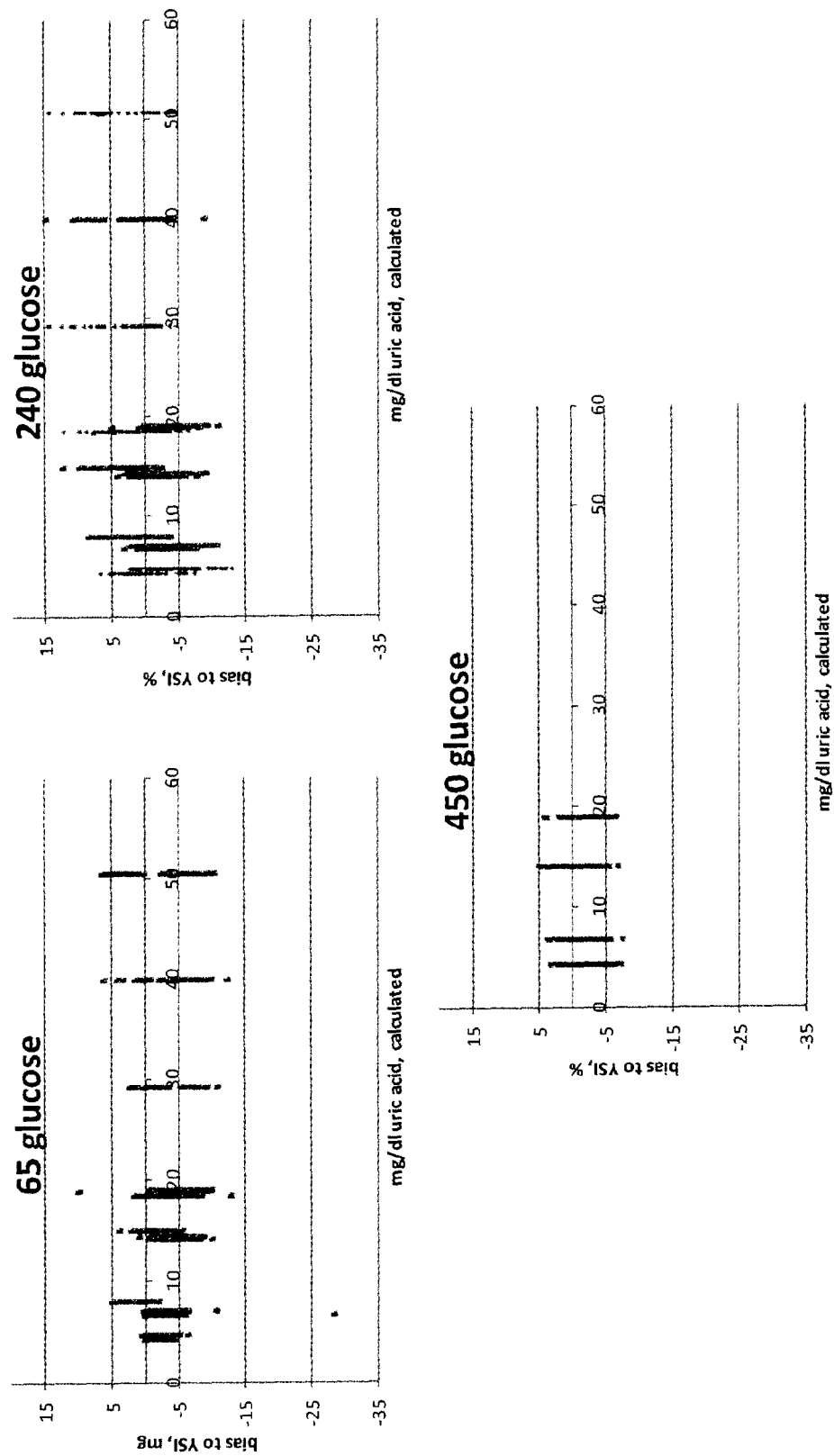
FIG. 10B are plots of the glucose concentration at the referential datum of 65 mg/dL; 240 mg/dL; and 450 mg/dL (nominal values) versus concentration calculated by the new technique and corrected for temperature variations at various levels of uric acid in the measured samples.

Comparing FIG. 9 with FIG. 8, it can be seen that the new technique virtually eliminates the substantial uric acid effect in $G_{basic}$ (or $G_1$ which is used interchangeably herein). Comparing FIG. 10A and Table IIA (using the pre-existing technique) with FIG. 10B and Table IIB (using the new technique with the data in the uric acid study), it can be seen that in the highest accuracy bracket, e.g., at 240 mg/dL at 10 mg (or 12%) and at 12 mg (or 15%), the performance improvement is dramatic, due to the elimination of bias trends. In the hematocrit study, a comparison can be made between FIG. 11A and Table IIIA (using the pre-existing technique) and FIG. 11B and Table IIIB (with the new technique), which shows that performance at normal uric acid is generally good and the overall improvement is small, but it can be seen that a definite trend is eliminated at high hematocrit.

As described herein, applicant has demonstrated that the pre-existing technique could be improved with respect to interfering reducing agents. Applicant has discovered how to (a) resolve the adjustment of $i_R$ for interfering reducing agent currents (i2corr) with respect to improved parameters, and (b) account for hematocrit with interfering reducing agent currents before being input into the hematocrit compensation function. After implementation of the improved technique, the percent of results within 10 mg or 12% of the YSI, even at the combined extremes of uric acid concentration and hematocrit, was demonstrated to be >99%. This shows that the Verio test strip/meter configuration, with the current dosing sequence, voltage profile and signal collection routine, is capable of significantly improved performance.

By virtue of the improved techniques described herein and with reference to FIG. 6, a method of determining highly accurate glucose concentration can be obtained by deriving an initial glucose proportional current based on first current, second current, and estimated current from the test cell (steps 602, 604, 606, 608, 610, and 612); calculate an initial glucose proportional current (step 614); formulating a hematocrit compensation factor based on the initial glucose proportional current (step 616); and calculating a glucose concentration from the derived initial glucose proportional current and the hematocrit compensation factor (step 618); thereafter, the result is displayed to the user (step 620) and the test logic returns to a main routine running in the background. The method specifically may involve inserting the test strip into a strip port connector of the test meter to connect at least two electrodes of the test strip to a strip measurement circuit; initiating a test sequence after deposition of a sample; applying a first voltage; initiating a change of analytes in the sample from one form to a different form and switching to a second voltage different than the first voltage; changing the second voltage to a third voltage different from the second voltage; measuring a second current output of the current transient from the electrodes after the changing from the second voltage to the third voltage; estimating a current that approximates a steady state current output of the current transient after the third voltage is maintained at the electrodes; calculating a blood glucose concentration based on the first, second and third current output of the current transient with Equations 13-16.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining blood glucose concentration with a glucose measurement system that includes a test strip and test meter, the test meter having a microcontroller programmed to apply a plurality of test voltages to the test strip and measure a current transient output resulting from an electrochemical reaction in a test chamber of the test strip, the method comprising:

inserting the test strip into a strip port connector of the test meter to connect at least two electrodes of the test strip to a strip measurement circuit;
initiating a test sequence after deposition of a sample;
applying a first voltage and measuring a first current for a first time duration;
switching the first voltage to a second voltage different than the first voltage;
changing the second voltage to a third voltage different from the second voltage;
measuring a second current output of a current transient from the electrodes after the changing from the second voltage to the third voltage;
estimating a third current that approximates a steady state current output of a current transient after the third voltage is maintained at the electrodes;
calculating a blood glucose concentration based on the first, second and third current outputs of the current transients with an equation of the form:

$$G_1 = \left(\frac{|i2corr'|}{|i'_L|}\right)^{p'} (a'|i2corr'| - zgr') + d;$$

where: $G_1$ is proportional to glucose concentration;

$$i_R = \sum_{t=4.4}^{t=5} i(t);$$

$$i'_L = \left(\sum_{t \sim 1.4 secs}^{t \sim 4 secs} i(t)\right) - 41(i_2);$$

$$i2corr' = \left(\frac{|i_{4.1}| + b'|i_5| - c|i_{1.1}|}{|i_{4.1}| + b'|i_5|}\right) i_R$$

where:
a' is approximately 0.14, b' is approximately 4.9, c is approximately 4.24, d is approximately 11.28, p' is approximately 0.548, and zgr' is approximately 9.38;
$i_{4.1}$ comprises the current measured during application of the third voltage;
$i_5$ comprises the current measured during application of the third voltage;
$i_{1.1}$ comprises the current measured during application of the second voltage; and
$i_2$ comprises the current measured during application of the second voltage.

2. The method of claim 1, in which the measuring of the first current output comprises measuring a current output of the at least two electrodes at about 1.1 seconds after initiation of the test sequence.

3. The method of claim 2, in which the measuring of the second current output comprises measuring a current output of the at least two electrodes at about 4.1 seconds after initiation of the test sequence.

4. The method of claim 2, in which the estimating of the steady state current output comprises measuring a current output of the at least two electrodes at about 5 seconds after initiation of the test sequence.

5. A blood glucose measurement system comprising:
an analyte test strip including:
a substrate having a reagent disposed thereon;
at least two electrodes proximate the reagent in test chamber;
an analyte meter including:
a strip port connector disposed to connect to the two electrodes;
a power supply; and
a microcontroller electrically coupled to the strip port connector and the power supply, the microcontroller programmed to determine a glucose concentration $G_1$ based on a hematocrit compensation factor and initial glucose proportional current in which the hematocrit compensation factor comprises a ratio that includes the initial glucose proportional current so that at least 97% of corrected test results are within respective bias criterion of ±10 mg/dL at 65 mg/dL, 240 mg/dL, or at 450 mg/dL as compared to reference YSI data; ±12 mg/dL at 65 mg/dL, 240 mg/dL, or 450 mg/dL as compared to reference YSI data; and ±15 mg/dL at 65 mg/dL, 240 mg/dL, or 450 mg/dL as compared to reference YSI data;
the test meter comprising a strip port connector of the test meter to connect at least two electrodes of the test strip to a strip measurement circuit, the strip measurement circuit having a microcontroller programmed to:
apply a plurality of test voltages to the test strip and measure a current transient output resulting from an electrochemical reaction in a test chamber of the test strip;
initiate a test sequence after deposition of a sample by applying a first voltage for a first time duration and measuring a first current;
switch the first voltage to a second voltage different than the first voltage;
change the second voltage to a third voltage different from the second voltage;
measure a second current output of a current transient from the electrodes after the changing from the second voltage to the third voltage;
estimate a third current that approximates a steady state current output of a current transient after the third voltage is maintained at the electrodes;
calculate a blood glucose concentration based on the first, second and third current outputs of the current transients with an equation of the form:

$$G_1 = \left(\frac{|i2corr'|}{|i'_L|}\right)^{p'} (a'|i2corr'| - zgr') + d;$$

Where: $G_1$ is proportional to glucose concentration;

$$i_R = \sum_{t=4.4}^{t=5} i(t);$$

$$i_L'' = \left(\sum_{t\sim 1.4 secs}^{t\sim 4 secs} i(t)\right) - 41(i_2);$$

$$i2corr' = \left(\frac{|i_{4.1}| + b'|i_5| - c|i_{1.1}|}{|i_{4.1}| + b'|i_5|}\right) i_R$$

where:
a' is approximately 0.14, b' is approximately 4.9, c is approximately 4.24, d is approximately 11.28, p' is approximately 0.548, and zgr' is approximately 9.38;
$i_{4.1}$ comprises the current measured during application of the third voltage;
$i_5$ comprises the current measured during application of the third voltage;
$i_{1.1}$ comprises the current measured during application of the second voltage; and
$i_2$ comprises the current measured during application of the second voltage.

* * * * *